US005667980A

United States Patent [19]

Pawson et al.

[11] Patent Number: 5,667,980
[45] Date of Patent: Sep. 16, 1997

[54] METHOD FOR ASSAYING FOR A SUBSTANCE THAT AFFECTS AN SH2 PHOSPHORYLATED LIGAND REGULATORY SYSTEM

[75] Inventors: Anthony Pawson; Michael Reedijk, both of Toronto, Canada

[73] Assignee: Mount Sinai Hospital Corporation, Toronto, Canada

[21] Appl. No.: 221,699

[22] Filed: Mar. 28, 1994

Related U.S. Application Data

[63] Continuation of Ser. No. 861,330, Mar. 31, 1992, abandoned, which is a continuation-in-part of Ser. No. 786,057, Oct. 31, 1991, Pat. No. 5,352,660.

[51] Int. Cl.$^6$ ............... C12Q 1/48; G01N 33/53; G01N 33/566; G01N 33/68
[52] U.S. Cl. ............... 435/7.8; 435/4; 435/15; 435/7.2; 435/7.21; 435/7.1; 435/7.6; 436/501
[58] Field of Search ............... 435/415, 7.2, 7.4, 435/7.8, 7.1, 7.6; 530/350, 352; 514/7; 436/501

[56] References Cited

U.S. PATENT DOCUMENTS

5,100,661 3/1992 Schmidt ............... 424/85.8

OTHER PUBLICATIONS

Cales, Nature (London) 332, 548, 1988.
Escobede et al., Cell 65, 75, 1991.
Otsu et al., Cell 65, 91, 1991.
Skolnik et al. Cell 65, 83, 1991.
Sadowski et al., Mol. Cell. Biol. 6, 4396, 1986.
Mayer et al., Nature 332, 272, 1988.
Mayer et al., Proc. Natl. Acad. Sci. U.S.A. 87, 2638, 1990.
Rodaway et al., Nature 342, 624, 1989.
Drubin et al., Nature 343, 288, 1990.
Kazlauskas and Cooper, EMBO J. 9, 3279, 1990.
Escobedo et al., Mol. Cell. Biol. 11, 1125, 1991.
Matsuda et al., Science, 248, 1537, 1990.
Mayer et al., Proc. Natl. Acad. Sci. 88, 627, 1991.
Kazlauskas et al Cell 58, 1121, 1989.
Taylor et al., EMBO J. 8, 2029, 1989.
Severinsson et al., Mol. Cell. Biol. 10, 801, 1990.
Escobedo and Williams, Nature 335, 85, 1988.
Reedijk et al., Mol. Cell. Biol. 10, 5601, 1990.
Shurtleff et al., EMBO J. 9, 2415, 1990.
Choudhury et al., J. Biol. Chem. 266, 8068, 1991.
Tapley et al., Mol. Cell. Biol. 10, 2528, 1990.
van der Geer and Hunter, Mol. Cell. Biol. 10, 2991, 1990.
Cantley et al., Cell 64, 281, 1991.
Downing et al., Mol. Cell. Biol. 11, 2489, 1991.
Declue, J. & Martin, G.S. (1989) J. Virol. 63, 542–554.
Koch, et al. (1989) Mol. Cell. Biol. 9, 4131–4140.
Ellis, C. et al (1990) Nature (London) 343,377–381.
Letwin et al., Oncogene 3, 621, 1988.
Liu and Pawson, Mol. Cell. Biol. 11, 2511–2516, 1991.
Marshall, M.S. et al (1989) EMBO. J. 8, 1105–1110.

Reynolds, A.B. et al. (1989) Mol. Cell. Biol. 9, 3951–3958.
Lau, A. F. (1986) Virology 151, 86–99.
Mayer et al (1988) (Cold Spring Harbor Symp. Quant. Biol. 53, 907–914.
Rothwell and Rohrschneider, Oncogene 1, 311–324, 1987.
Ullrich and Schlessinger, Cell 61, 203, 1990.
Pawson and Bernstein, Trends Gen. 6, 350, 1990.
Chen et al., Nature 328, 820, 1987.
Honneger, Mol. Cell. Biol. 7, 4568, 1987.
Williams, Science 243, 1564, 1989.
Yarden and Schlessinger, Biochemistry 26, 1434, 1987.
Böni–Schnetzler and Pilch, Proc. Natl. Acad. Sci. U.S.A. 84, 7832, 1987.
Heldin et al., J. Biol. Chem. 264, 8905, 1989.
Kazlauskas and Cooper, Cell 58, 1121, 1989.
Coughlin et al., Science 243, 1191, 1989.
Kazlauskas et al., Science 247, 1578, 1990.
Pawson, T., Oncogene 3, 1988.
Veillette et al., Cell 55, 301, 1988.
Rudd et al., Proc. Natl. Acad. Sci. U.S.A. 85, 5190, 1988.
Shaw et al., Cell 59, 627, 1989.
Kypta et al., Cell 62, 481, 1990.
Ralston and Bishop, Proc. Natl. Acad. Sci. U.S.A. 82, 7845, 1985.
Gould and Hunter, Mol. Cell. Biol. 8, 3345, 1988.
Hunter and Cooper, Annu. Rev. Biochem. 54, 897, 1985.
Margolis et al, Cell 57 1101, 1989.

(List continued on next page.)

*Primary Examiner*—Robert A. Wax
*Assistant Examiner*—Rebecca Prouty
*Attorney, Agent, or Firm*—Bereskin & Parr

[57] ABSTRACT

A method for assaying a medium for the presence of a substance that affects an SH2-phosphorylated ligand regulatory system. The method employs an SH2-like domain or a subdomain thereof and a phosphorylated ligand. The phosphophorylated ligand is capable of interacting with the SH2-like domain or a subdomain thereof to form an SH2-phosphorylated ligand complex. The SH2-like domain or subdomain and/or the phosphorylated ligand are present in a known concentration. The SH2-like domain or a subdomain thereof and the phosphorylated ligand are incubated with a substance which is suspected of affecting an SH2-phosphorylated ligand regulatory system. The method is carried out under conditions which permit the formation of the SH2-phosphorylated ligand complex. SH2-phosphorylated ligand complex, free SH2-like domain or subdomains thereof, or non-complexed phosphorylated ligand are assayed. The invention also relates to an isolated SH2-phosphorylated ligand complex; a method of using an isolated SH2-like domain or a subdomain thereof to screen for phosphorylated ligands which are active in an SH2-phosphorylated ligand regulatory system; a method of using an isolated SH2-like domain or a subdomain thereof to regulate the interaction of a signalling protein with a related phosphorylated ligand; and a pharmaceutical composition comprising an isolated SH2-like domain or a subdomain thereof for use as an agohist or antagonist of the interaction of a signalling protein with a related phosphorylated ligand.

10 Claims, 20 Drawing Sheets

OTHER PUBLICATIONS

Meisenhelder et al., Cell 57, 1109, 1989.
Kaplan et al., Cell 61, 125, 1990.
Morrison et al., Cell 58, 649, 1989.
Morrison et al., Proc. Natl. Acad.Sci. U.S.A. 85, 8855, 1988.
Rhee et al., Science 244, 546, 1989.
Margolis et al., Science 248, 607, 1990.
Whitman et al, Nature 332, 644, 1988.
Kaplan et al., Cell 50, 1021, 1987.
Courtneidge and Heber, Cell 50, 1031, 1987.
Fukui and Hanafusa, Mol. Cell. Biol. 9, 1651, 1989.
Carpenter et al., J. Biol. Chem. 265, 19704, 1990.
Auger et al., Cell 57, 167, 1989.
Varticovski et al., Nature 342, 699, 1989.
Adari et al., Science 240, 518, 1988.
H. Hirai "Function of SH2 Domain of C–SCC" Jikken Igaku 9(9) 1046–1051 (Jul. 1991).
M. Matsuda "Function of SH2/SH2' Region . . . " Jikken Igaku 8(17) 2239–2243 (Dec. 1990).
Anderson, D. et al. "Binding of SH2 Domains fo Phospholipase Cy1 . . . " Science vol. 250:979–982 (Nov. 1990).
Moran, M.F. et al. "Src Homology Region 2 Domains Direct . . . " Proc. Natl. Acad. Sci. 87:8622–8626 (Nov. 1990).
Koch, C.A. et al. "SH2 and SH3 Domains: Elements That Control . . . " Science vol. 252:668–674 (May 1991).
Matsuda, M. et al. "Identification of Domains of the v–crK . . . " Mol. Cell. Biol. 11(3) 1607–1613 (Mar. 1991).

FIGURE 2

METHOD FOR ASSAYING FOR A SUBSTANCE THAT AFFECTS AN SH2 PHOSPHORYLATED LIGAND REGULATORY SYSTEM

This application is a continuation of U.S. Ser. No. 07/861,330 filed Mar. 31, 1992, now abandoned, which in turn, is a continuation-in-part of U.S. Ser. No. 07/786,057 filed Oct. 31, 1991, now U.S. Pat. No. 5,382,660.

FIELD OF THE INVENTION

The invention relates to a method for assaying a medium for the presence of a substance that affects an SH2-phosphorylated ligand regulatory system; an isolated SH2-phosphorylated ligand complex; a method of using an isolated SH2-like domain or a subdomain thereof to screen for phosphorylated ligands; a method of using an isolated SH2-like domain or a subdomain thereof to regulate the interaction of a signalling protein with a related phosphorylated ligand; and a pharmaceutical composition comprising an isolated SH2-like domain or a subdomain thereof.

BACKGROUND OF THE INVENTION

A common mechanism by which growth factors regulate cellular proliferation and differentiation is through transmembrane receptors with inducible protein-tyrosine kinase activity (Ullrich and Schlessinger, Cell 61, 203 (1990); Pawson and Bernstein, Trends Gen. 6, 350 (1990)). Indeed the mitogenic effects of growth factors such as epidermal growth factor (EGF) or platelet-derived growth factor (PDGF) absolutely require the tyrosine kinase activity of their receptors (Chen et al., Nature 328, 820 (1987); Honneger, Mol. Cell. Biol. 7, 4568 (1987); Williams, Science 243, 1564 (1989)). Growth factors induce receptors to cluster, which is followed by intermolecular tyrosine phosphorylation of the oligomerized receptors (Yarden and Schlessinger, Biochemistry 26, 1434 (1987); Boni-Schnetzler and Pilch, Proc. Natl. Acad. Sci. U.S.A. 84, 7832 (1987); Heldin et al., J. Biol. Chem. 264, 8905 (1989)). Autophosphorylation of the PDGF receptor (PDGFR) is important both for its subsequent interactions with substrates and for the induction of DNA synthesis (Kazlauskas and Cooper, Cell 58, 1121 (1989); Coughlin et al., Science 243, 1191 (1989); Kazlauskas et al., Science 247, 1578 (1990)).

A second group of tyrosine kinases, for which Src, Fps, and Abl are the prototypes, are entirely intracellular (Pawson, T., Oncogene 3, 491 (1988)). In the case of the Src-like tyrosine kinase Lck, which is specifically expressed in T cells, the $NH_2$-terminal region of the kinase associates with the short cytoplasmic tails of the cell adhesion molecules CD4 and CD8 (Veillette et al., Cell 55, 301 (1988); Rudd et al., Proc. Natl. Acad. sci. U.S.A. 85, 5190 (1988); Shaw et al., Cell 59, 627 (1989)). In addition, Src and the related kinases Fyn and Yes physically associate with, and are phosphorylated by, the β-PDGFR (Kypta et al., Cell 62, 481 (1990)). PDGF stimulation is associated with a three- to five-fold increase in Src kinase activity, which may serve to amplify the tyrosine kinase signal (Kypta et al., Cell 62, 481 (1990); Ralston and Bishop, Proc. Natl. Acad. Sci. U.S.A. 82, 7845 (1985); Gould and Hunter, Mol. Cell. Biol. 8, 3345 (1988)). Hence, the Src-like kinases also appear to participate in signal transduction.

Many structural alterations have been documented for both receptor-like and cytoplasmic tyrosine kinases, which induce constitutive tyrosine kinase activity and simultaneously activate oncogenic potential (Ullrich and Schlessinger, Cell 61, 203 (1990); Pawson and Bernstein, Trends Gen. 6, 350 (1990); Hunter and Cooper, Annu. Rev. Biochem. 54, 897 (1985)). The biological activities of transforming tyrosine kinases, like their normal counterparts, are generally dependent on their kinase activity.

After stimulation with PDGF or EGF several proteins become physically associated with, and phosphorylated by, the activated PDGFR or EGF receptor (EGFR). A number of these receptor-binding proteins have been identified, including phosphoinositide-specific phospholipase C(PLC)-γ1 (Margolis et al, Cell 57 1101 (1989); Meisenhelder et al., ibid., p. 1109), p21$^{ras}$ GTPase-activating protein (GAP) (Kazlauskas et al., Science 247, 1578 (1990); Kaplan et al., ibid. 61, 121 (1990)), phosphatidylinositol (PI) 3'-kinase (PI3K) (Kazlauskas and Cooper, Cell 58, 1121 (1989); Coughlin et al., Science 243, 1191 (1989)), Src and Src-like tyrosine kinases (Kypta et al., Cell 62, 481 (1990)), and Raf (Morrison et al., ibid. 58, 649 (1989); Morrison et al., Proc. Natl. Acad. Sci. U.S.A. 85, 8855 (1988)). These associated proteins are likely targets of receptor activity.

PLC-γ1 is one of several PLC isoforms that cleaves the phospholipid phosphatidylinositol 4,5-bisphosphate ($PIP_2$) to the second messengers diacyglycerol and inositol triphosphate, which in turn stimulate protein kinase C and raise intracellular calcium (Rhee et al., Science 244, 546 (1989)). PDGF stimulates PI turnover in cells where PLC-γ1 is the principal PLC isoform (Margolis et al., Cell 57, 1101 (1989); Meisenhelder et al., ibid., p. 1109), and overexpression of PLC-γ1 enhances the accumulation of inositol phosphates in response to PDGF (Margolis et al., ibid. 248, 607 (1990)). Thus, PLC-γ may couple PDGF stimulation to the breakdown of $PIP_2$.

PI3K phosphorylates the inositol ring of PI in the D-3 position (Whitman et al, Nature 332, 644 (1988)). PI3K activity is associated with a variety of activated tyrosine kinases and correlates with the presence of a tyrosine phosphorylated 85-kilodalton (kD) protein (p85) (Kaplan et al., Cell 50, 1021 (1987); Courtneidge and Heber, ibid., p. 1031; Fukui and Hanafusa, Mol. Cell. Biol. 9, 1651 (1989)). Purified PI3K is a heterodimeric complex that contains p85 and a 110-Kd protein (p110) (Carpenter et al., J. Biol. Chem. 265, 19704 (1990)). The purified p85 subunit has no detectable PI3K activity, but binds tightly to activated PDGFR or EGFR in vitro. PDGF stimulation induces accumulation of $PI-3,4-P_2$ and $PI-3,4,5-P_3$, confirming that PI3K is regulated by tyrosine kinases in vivo (Auger et al., ibid. 57, 167 (1989). Stimulation of cells with PDGF or CSF-1 leads to the formation of phosphoinositides which are phosphorylated at the D-3 position of the inositol ring, suggesting that these growth factors stimulate PI 3'-kinase activity in vivo (Auger et al., Cell 57, 167 (1989); Varticovski et al., Nature 352, 699 (1989).

GAP stimulates the ability of p21$^{ras}$ (Ras) to hydrolyze GTP to GDP (guanosine diphosphate) (B. Margolis et al., ibid. 248, 607 (1990)) and thereby acts as a negative regulator by returning Ras from the active GTP-bound state to the inactive GDP-bound conformation. GAP interacts with the presumed effector region of p21$^{ras}$ (Adari et al., Science 240, 518 (1988); Cales, Nature (London) 332, 548 (1988)) suggesting that it might also be the Ras target or might modify the association of p21$^{ras}$ with its target.

Raf is a protein-serine/threonine kinase that complexes with the PDGFR after PDGF stimulation, although it is unclear whether this is a direct interaction (Morrison et al., ibid. 58, 649 (1989); Morrison et al., Proc. Natl. Acad. Sci. U.S.A. 85, 8855 (1988)). Several unidentified polypeptides have also been found to bind to activated PDGFR (Kazlauskas and Cooper, Cell 58, 1121 (1989); Coughlin et al., Science 243, 1191 (1989); Kazlauskas and Cooper, EMBO J. 9, 3279 (1990)).

The proteins that associate with activated growth factor receptors have quite distinct enzymatic properties and are structurally unrelated within their catalytic domains. However, with the exception of Raf they share conserved noncatalytic domains termed Src homology (SH) regions 2, and 3 (see FIG. 1 where 3 represents SH-3 domain; Ras GA the Ras GTPase activating region of GAP; PLC the catalytic sequences of PLC-γ1; gag, retroviral coat protein sequence; CYS, cysteine rich domain of Vav; LEU, leucine-rich region of Vav). cDNAs for two isoforms of p85 of PI3K have been sequenced, and shown to encode closely related proteins with two SH2 domains (Escobede et al., Cell 65, 75, (1991); Otsu et al., Cell 65, 91 (1991); Skolnik et al. Cell 65, 83 (1991)). The SH2 domain is a sequence of ~100 amino acids, originally identified in the vFps and vSrc cytoplasmic tyrosine kinases by virtue of its effects on both catalytic activity and substrate phosphorylation (T. Pawson, Oncogene 3, 491 (1988) and I. Sadowski et al., Mol. Cell. Biol. 6, 4396 (1986)).

An SH2 sequence has also been identified in the v-Crk oncoprotein, which complexes with several tyrosine phosphorylated proteins in crk-transformed cells (Mayer et al., Nature 332, 272 (1988); Mayer and Hanafusa, Proc. Natl. Acad. Sci. U.S.A. 87, 2638 (1990)). Most SH2-containing proteins also contain a motif, SH3, which is found independently in several cytoskeletal proteins and may mediate interactions with the cytoskeleton (Pawson, Oncogene 3, 491 (1988); Mayer et al., Nature 332, 272 (1988); Mayer and Hanafusa, Proc. Natl. Acad. Sci. U.S.A. 87, 2638 (1990); Rodaway et al., Nature 342, 624 (1989); Drubin et al., Nature 343, 288 (1990)).

Receptor autophosphorylation may create high affinity binding sites for SH2-containing proteins. Substitution of the Tyr751 autophosphorylation site in the human βPDGF receptor (PDGFR) with phenylalanine decreases PDGF-induced association with PI 3'-kinase (Kazlauskas and Cooper, EMBO J. 9, 327 (1990); Kazlauskas et al., Science 246, 1578 (1990)). A tyrosine phosphorylated peptide spanning the corresponding site of the mouse βPDGFR blocks association of the activated receptor with PI 3'-kinase in vitro (Escobedo et al., Mol. Cell. Biol. 11, 1125 (1991). In general, tyrosine phosphorylation of cellular proteins is important for their stable association with SH2 domains in vitro (Matsuda et al., Science, 248, 1537 (1990); Mayer et al., Proc. Natl. Acad. Sci. 88, 627 (1991)).

The autophosphorylation sites of growth factor receptors are frequently contained in non-catalytic regions located within or adjacent to the kinase domain. The PDGFR subfamily of receptor tyrosine kinases, which includes α and βPDGFRs, the macrophage colony stimulating factor receptor (CSF-1R) and c-Kit, the receptor for Steel factor, each contain a sequence of between 70 and 100 residues which interrupts the kinase domain. This sequence, called the kinase insert region (KI) is dispensable for kinase activity (Taylor et al., EMBO J. 8, 2029 (1989); Severinsson et al., Mol. Cell. Biol. 10, 801 (1990); Escobedo and Williams, Nature 335, 85 (1988)) but is required for efficient PI 3'-kinase binding (Couglin et al., Science 243, 1191 (1989); Kazlauskas et al., Cell 58, 1121 (1989); Reedijk et al., Mol. Cell. Biol. 10, 5601 (1990); Shurtleff et al., EMBO J. 9, 2415 (1990); Choudhury et al., J. Biol. Chem. 266, 8068 (1991)). The kinase insert contains demonstrated autophosphorylation sites, including Tyr751 in the human βPDGFR (Kazlauskas et al., Cell 58, 1121 (1989)), and Tyr697 and Tyr706 in the mouse CSF-1R (Tapley et al., Mol. Cell. Biol. 10, 2528 (1990); van der Geer and Hunter, Mol. Cell. Biol. 10, 2991 (1990)). Tyr751 and surrounding amino acids in the βPDGFR conform to a proposed consensus binding sequence for PI 3'-kinase, consisting of a phosphorylated tyrosine within the context (Asp/Glu)-(Asp/Glu)-P.Tyr-(Met/Val)-(Pro/Asp/Glu)-Met (Cantley et al., Cell 64, 281 (1991)).

Although they have not been identified as in vivo autophosphorylation sites, the sequence surrounding Tyr721 of the mouse CSF-1R KI and Tyr740 of the human βPDGFR KI also conform to this consensus and are presumptive PI 3'-kinase binding sites. A peptide containing the mouse homologue of human βPDGFR residue 740 inhibits PI 3'-kinase association with the receptor, provided this site is tyrosine phosphorylated (Escobedo et al., Mol. Cell. Biol. 11, 1125 (1991)). Deletion of the CSF-1R KI has been found to result in a profound decrease in the ability of the receptor to associate with PI 3'-kinase in CSF-1 stimulated cells (Reedijk et al., Mol. Cell. Biol. 10, 5601 (1990); Shurtleff et al., EMBO J. 9, 2415 (1990); Coudhury et al., J. Biol. Chem. 266, 8068 (1991)). Preincubation of activated CSF-1R with antibodies raised against a KI peptide containing residues corresponding to 699–719 in mouse CSF-1R has been found to reduce the ability of the receptor to associate with PI 3'-kinase (Downing et al., Mol. Cell. Biol. 11, 2489 (1991)).

SUMMARY OF THE INVENTION

The present inventors have determined by direct evidence that SH2 domains can mediate the interactions of diverse signalling proteins including cytoplasmic protein tyrosine kinases, p21$^{ras}$ GTPase-activating protein (GAP), phospholipase Cγ and the V-Crk oncoprotein, with a related set of phosphotyrosine ligands, including the epidermal growth factor (EGF) receptor. In particular, the present inventors have found that in Src-transformed cells GAP forms heteromeric complexes, notably with a highly tyrosine phosphorylated 62-kDa protein (p62). The stable association between GAP and p62 can be specifically reconstituted in vitro by using a bacterial polypeptide containing only the N-terminal GAP SH2 domain. The efficient phosphorylation of p62 by the v-Src or v-Fps tyrosine kinases depends, in turn, on their SH2 domains and correlates with their transforming activity. In lysates of EGF-stimulated cells, the N-terminal GAP SH2 domain binds to both the EGF receptor and p62. Fusion proteins containing GAP or v-Crk SH2 domains complex with similar phosphotyrosine proteins from src-transformed or EGF-stimulated cells but with different efficiencies. SH2 sequences, therefore, form autonomous domains that direct signalling proteins, such as GAP, to bind specific phosphotyrosine-containing polypeptides. By promoting the formation of these complexes, SH2 domains are ideally suited to regulate the activation of intracellular signalling pathways by growth factors.

The inventors have most importantly found that the SH2 domains of cytoplasmic signalling proteins such as PLCγ1, GAP, Src and Crk are sufficient for in vitro binding to activated growth factor receptors. In particular, the inventors found that the SH2 domains of PLCγ1 synthesized individually in bacteria formed high affinity complexes with the epidermal growth factor (EGF)-or platelet derived growth factor (PDGF)-receptors in cell lysates, and bound synergistically to activated receptors when expressed together as one bacterial protein. In vitro complex formation was dependent on prior growth factor stimulation and was competed by intracellular PLCγ1. Similar results were obtained for binding of GAP SH2 domains to the PDGF-receptor. The isolated SH2 domains of other signalling proteins, such as p60$^{src}$ and Crk, also bound activated PDGF-receptors in vitro.

The use of a specialized non-catalytic domain to direct complex formation between protein kinases and their presumptive targets is unprecedented.

The present inventors have also expressed the KI of the PDGFR on its own in bacteria and has shown that it possesses an intrinsic ability to bind PI 3'-kinase, which is greatly enhanced when it is phosphorylated on tyrosine. Mutagenesis studies of the KI of CSE-IR indicated that phosphorylation of Tyr721, within a predicted binding consensus sequence, is critical for PI 3'-kinase association.

The present inventors have also shown that the two SH2 domains of the p85 receptor binding subunit of PI 3'kinase mediate the interaction of PI 3'-kinase with the CSF-1R KI. In particular the present inventors have found that the tyrosine phosphorylated CSF-1R KI bound directly to the SH2 domains of the p85α regulatory subunit of PI 3'-kinase. In these experiments, both the CSF-1R KI and the p85α SH2 domains were expressed and isolated as bacterial fusion proteins. Hence, the phosphorylated KI of the CSF-1R and the SH2 domains of p85 contain all the structural information required for the formation of a stable complex. The CSF-1R and PI 3'-kinase have therefore evolved complementary non-catalytic domains that allow for their phosphorylation-dependent association. This is likely to be a general feature of the interactions of receptor tyrosine kinases with their targets.

Efficient in vitro binding of p85α SH2 domains was also found to be induced by tyrosine phosphorylation of the KI. In particular, phosphorylation of Tyr721 within the KI is critical for SH2 binding, whereas phosphorylation of Tyr697 and Tyr706 is neither necessary nor sufficient for stable association with the p85α SH2 domains. These results imply that the ability of PI 3'-kinase to bind to the phosphorylated CSF-1R in vivo depends on the recognition of a site encompassing Tyr721 by the p85 SH2 domains. The specificity with which PI 3'-kinase binds to this site is apparently an intrinsic property of the p85α SH2 domains. Complex formation between the CSF-1R and PI 3'kinase can therefore be reconstructed in vitro in a specific interaction involving the phosphorylated receptor KI and the SH2 domains of p85.

The finding that SH2 domains mediate the interactions of phosphorylated ligands with signalling proteins which regulate pathways that control gene expression, cell division, cytoskeletal architecture and cell metabolism permits the identification of substances which affect the interactions of phosphorylated ligands with signalling proteins and accordingly may be used in the treatment of conditions involving perturbation of signalling pathways. For example, it may be possible to identify substances which block an SH2-containing oncoprotein, or SH2 signalling protein or the actions of deregulated tyrosine kinases which interact with specific SH2 signalling proteins, and that may be useful in preventing transformation activity. In particular, in the case of cancers where there are deregulated tyrosine kinases, such as thyroid, breast carcinoma, stomach cancer and neuroblastoma, the method of the invention would permit the identification of substances which interfere with the binding of SH2 signalling proteins and the deregulated tyrosine kinase. In the case of cancers such as chronic myelogenous leukemia (CML) and acute lymphocytic leukemia (ALL), an SH2-containing oncoprotein interacts with a signalling protein which is autophosphorylated on serine resulting in transformation. The method of the present invention could be used to identify substances which interfere with the interaction and which may be useful in the treatment of CML and ALL.

Therefore, the present invention relates to a method for assaying a medium for the presence of a substance that affects an SH2-phosphorylated ligand regulatory system comprising providing an SH2-like domain or a subdomain thereof, and a phosphorylated ligand which is capable of interacting with said SH2-like domain or a subdomain thereof to form an SH2-phosphorylated ligand complex, said SH2-like domain or subdomain thereof and/or said phosphorylated ligand being present in a known concentration, and incubating with a substance which is suspected of affecting an SH2-phosphorylated ligand regulatory system, under conditions which permit the formation of said SH2-phosphorylated ligand complex, and assaying for said SH2-phosphorylated ligand complex, free SH2-like domain or subdomain thereof, or non-complexed phosphorylated ligand.

In a preferred embodiment of the invention, a method is provided for assaying a medium for the presence of an agonist or antagonist substance of an SH2-phosphorylated ligand regulatory system comprising providing an SH2-like domain or a subdomain thereof, and a phosphorylated ligand which is capable of interacting with said SH2-like domain or a subdomain thereof to form an SH2-phosphorylated ligand complex, said SH2-like domain or subdomain thereof and/or said phosphorylated ligand being present in a known concentration, and incubating with a suspected agonist or antagonist substance, under conditions which permit the formation of said SH2-phosphorylated ligand complex, and assaying for said SH2-phosphorylated ligand complex, free SH2-like domain or subdomains thereof, or non-complexed phosphorylated ligand.

The invention also provides a method for screening for antagonists that inhibit the affects of agonists of an SH2-phosphorylated ligand regulatory system. Thus, a substance that competes for the same binding site on the phosphorylated ligand or on the SH2-like domain or a subdomain thereof may be assayed.

The invention further provides an isolated SH2-phosphorylated ligand complex comprising an SH2-like domain or a subdomain thereof and a phosphorylated ligand which is capable of interacting with said SH2-like domain or a subdomain thereof.

The invention still further provides a method of using an isolated SH2-like domain or a subdomain thereof to screen for phosphorylated ligands which are active in an SH2-phosphorylated ligand regulatory system.

The invention also relates to a method of using an isolated SH2-like domain or a subdomain thereof to regulate the interaction of a signalling protein with a related phosphorylated ligand and a pharmaceutical composition comprising an isolated SH2-like domain or a subdomain thereof for use as an agonist or antagonist of the interaction of a signalling protein with a related phosphorylated ligand.

BRIEF DESCRIPTION OF THE DRAWINGS

The invention will be better understood with reference to the drawings in which:

FIG. 2 shows the amino acid sequences of several known SH2 domains;

DETAILED DESCRIPTION OF THE INVENTION

Figure 1:
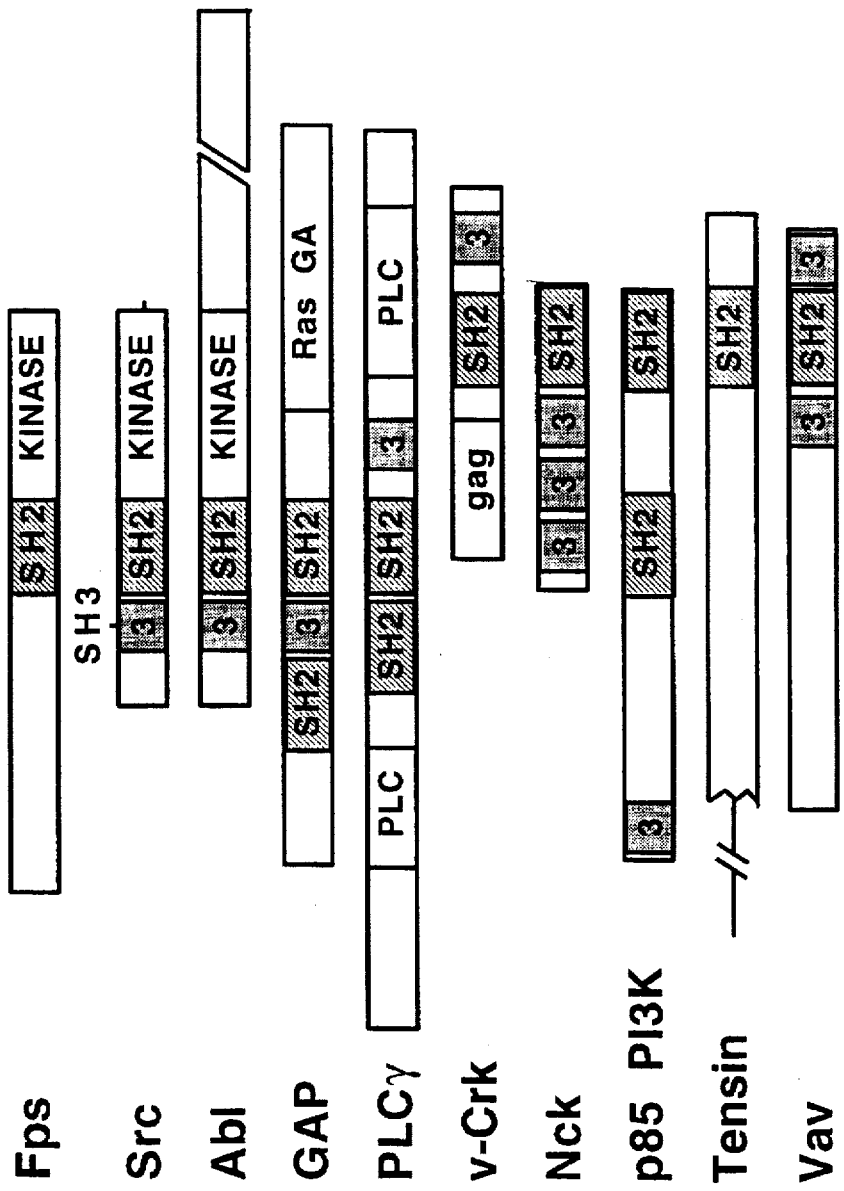
FIG. 1 shows the locations of SH2 domains of signalling proteins.

As hereinbefore mentioned the invention relates to a method for assaying a medium for the presence of a substance that affects an SH2-phosphorylated ligand regulatory system comprising providing an SH2-like domain or a subdomain thereof, and a phosphorylated ligand which is capable of interacting with said SH2-like domain or a subdomain thereof to form an SH2-phosphorylated ligand complex, said SH2-like domain or subdomain and/or said phosphorylated ligand being present in a known concentration, and incubating with a substance which is suspected of affecting an SH2-phosphorylated ligand regulatory system, under conditions which permit the formation of said SH2-phosphorylated ligand complex, and assaying for said SH2-phosphorylated ligand complex, free SH2-like domain or subdomains thereof, or non-complexed phosphorylated ligand.

In a preferred embodiment a method is provided for assaying a medium for the presence of an agonist or antagonist substance of an SH2-phosphorylated ligand regulatory system comprising providing an SH2-like domain or a subdomain thereof, and a phosphorylated ligand which is capable of interacting with said SH2-like domain or a subdomain thereof to form an SH2-phosphorylated ligand complex, said SH2-like domain or subdomain and/or said phosphorylated ligand being present in a known concentration, and incubating with a suspected agonist or antagonist substance, under conditions which permit the formation of said SH2-phosphorylated ligand complex, and assaying for said SH2-phosphorylated ligand complex, free SH2-like domain or subdomains thereof, or non-complexed phosphorylated ligand.

The invention further provides an isolated SH2-phosphorylated ligand complex comprising an SH2-like domain or a subdomain thereof and a phosphorylated ligand which is capable of interacting with said SH2-like domain or a subdomain thereof.

The invention still further provides a method of using an isolated SH2-like domain or a subdomain thereof to screen for phosphorylated ligands which are active in an SH2-phosphorylated ligand regulatory system.

The invention also relates to a method of using an isolated SH2-like domain or a subdomain thereof to regulate the interaction of a signalling protein with a related phosphorylated ligand and a pharmaceutical composition comprising an isolated SH2-like domain or a subdomain thereof for use as an agonist or antagonist of the interaction of a signalling protein with a related phosphorylated ligand.

The term "SH2-like domain or a subdomain thereof" refers to a sequence which is substantially homologous to a Src homology region 2 (SH2 region), or a subdomain of an SH region preferably a conserved region of an SH region. The Src homology region is a noncatalytic domain of ~100 amino acids which was originally identified in the Vfps and Vsrc cytoplasmic tyrosine kinases by virtue of its affects on both catalytic activity and substrate phosphorylation (T. Pawson, Oncogene 3, 491 (1988) and I. Sadowski et al., Mol. Cell. Biol. 6, 4396 (1986)). An SH2 sequence has also been identified in the v-Crk oncoprotein, which complexes with several tyrosine phosphorylated proteins in crk-transformed cells (Mayer et al., Nature 332, 272 (1988); Mayer and Hanafusa, Proc. Natl. Acad. Sci. U.S.A. 87, 2638 (1990)).

The sequences of several known SH2 domains are aligned in FIG. 2. In FIG. 2, residues that are conserved within at least three subfamilies of SH2 domains are capitalized and shaded. Residues that are conserved within one or two groups are capitalized. Residues that are poorly or not at all conserved are in lowercase. Invariant residues are indicated by asterisks. Conserved basic amino acids that might participate in interactions with phosphotyrosine are arrowed. Conserved motifs I to V are indicated by solid lines, whereas the connecting variable regions i to iv are indicated by broken lines. The suffix N indicates the more $NH_2$-terminal SH2 domain of PLC-γ, GAP or p85 whereas C indicates the more COOH-terminal domain. The SH2 domain of two isoforms of PLC-γ (γ1 and γ2) and p85 (α and β) are shown (Otsu et al., Cell 65, 91 (1991)). Sequences were aligned by eye. Abbreviations for the amino acid residues are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp;.and Y, Tyr.

An inspection of the aligned SH2 sequences reveals the presence of five well-conserved sequence motifs (designated I to V in FIG. 2), which are separated by more variable sequence elements (i to iv). The variable regions generally contain one or more glycine or proline residues, suggesting that they form turns or hinges that connect the conserved subdomains.

The identification of SH2-like domains may be accomplished by screening a cDNA expression library with a phosphorylated ligand with high affinity to SH2 domains (e.g. the autophosphorylated COOH-terminal tail to the EGFR) to isolate cDNAs for SH2 proteins. An SH2-like domain which binds to a specific phosphorylated ligand may be identified by screening a cDNA expression library with the specific phosphorylated ligand. One could use PCR (Wilks, A. F., Proc. Natl. Acad. Sci. U.S.A. Vol. 86, pp. 1603–1607, March 1989) or low stringency screening (Hanks, S. K., Proc. Natl. Acad. Sci. U.S.A. Vol. 84, pp 388–392, January 1987) with an SH2 specific probe.

The term "phosphorylated ligand" refers to a phosphorylated polypeptide or peptide that is capable of interacting with an SH2-like domain or a subdomain thereof, and includes phosphotyrosine, and phosphoserine/phosphothreonine-containing peptides or polypeptides. Examples of phosphorylated ligands which may be utilized in the method of the invention are SH2 binding sites or mimetics therof, in particular the SH2 binding sites on transmembrane receptors with inducible protein-tyrosine kinase activity and cytoplasmic tyrosine phosphorylated proteins.

A phosphorylated ligand may be identified by reacting an SH2 domain(s) of a specific regulatory protein with a suspected SH2 binding site which has been expressed and phosphorylated in a host cell, and determining binding activity. In a preferred method a tyrosine phosphorylated ligand may be identified by expressing a sequence encoding residues of a suspected phosphorylated ligand as a fusion protein, preferably a TrpE fusion protein, in a host cell, preferably a microorganism, most preferably *Escherichia coli*; inducing tyrosine phosphorylation of the fusion protein by infecting the host cell with a vector encoding the cytoplasmic domain of a protein tyrosine kinase, preferably the λgtII bacteriophage encoding the cytoplasmic domain of the Elk tyrosine kinase (λB1-Elk); isolating host cells capable of expressing the fusion protein and the vector as a lysogen; labelling the host cell preferably with [$^{32}$P]orthophosphate; sequentially inducing the fusion protein and the tyrosine kinase; immunoprecipitating labelled lysates with antibodies to the fusion protein, preferably anti-TrpE antibodies (αTrpE), separating the immune complexes and subjecting to autoradiography and phosphoamino acid analysis. Once tyrosine phosphorylation of the suspected ligand has been identified, it can be assayed for its binding to an SH2 domain, isolated for example as a GST fusion protein. Using this method complementary phosphorylated ligands and SH2-like domains or subdomains may be identified.

It will be appreciated that the selection of an SH2-like domain or subdomain thereof and a phosphorylated ligand in the method of the invention will depend on the nature and expected utility of the substance to be assayed. It will also be appreciated that the selection of a specific complementary phosphorylated ligand and SH2-like domain or subdomain in the method of the invention will allow for the identification of a specific substance that affects a specific SH2-phosphorylated ligand regulatory system. Thus, the identification of the specific complex formed between phosphorylated receptor KI of CSF-1R and the SH2 domains of p85 of PI 3'-kinase by the present inventor allows the identification of specific substances that affect the interaction of CSF-1R and PI 3'-kinase.

The phosphorylated ligand is preferably synthetically constructed having regard to the interaction of the phosphorylated ligand with a particular SH2 domain.

The term "SH2-phosphorylated ligand regulatory system" used herein refers to the interactions of an SH2-like domain or a subdomain thereof and a phosphorylated ligand and includes the binding of an SH2-like domain or a subdomain thereof to a phosphorylated ligand or any modifications to the SH2-like domain or a subdomain thereof or to the phosphorylated ligand associated therewith, to form an SH2/ligand complex thereby activating a series of regulatory pathways that control gene expression, cell division, cytoskeletal architecture and cell metabolism. Examples of such regulatory pathways are the GAP/Ras pathway, the pathway that regulates the breakdown of polyphosphoinositides through phospholipase C (PLC), and the Src/tyrosine kinase pathway.

The term "signalling protein" used herein includes cytoplasmic protein tyrosine kinases, p21$^{ras}$ GTPase-activating protein (GAP), phospholipase Cγ and the V-Crk oncoprotein, phosphatidylinositol (PI) 3'-kinase (PI3K), Src and Src-like tyrosine kinases, and Raf.

The invention may be used to assay for a substance that affects the interaction of an SH2-like domain or a subdomain thereof and a phosphorylated ligand, preferably a suspected agonist or antagonist. The agonist or antagonist may be an endogenous physiological substance or it may be a natural or synthetic drug.

The SH2-phosphorylated ligand complex, free SH2-like domain or subdomains thereof, or non-complexed phosphorylated ligand in the methods of the invention may be isolated by conventional isolation techniques, for example, salting out, chromatography, electrophoresis, gel filtration, fractionation, absorption, polyacrylamide gel electrophoresis, agglutination, or combinations thereof.

The assaying for SH2-phosphorylated ligand complex, free SH2-like domain or subdomains thereof, or non-complexed phosphorylated ligand in the method of the invention may be carried out using known methods. To facilitate the assay of the components, antibody against the SH2-like domain or a subdomain thereof or the phosphorylated ligand, or a labelled SH2-like domain or a subdomain thereof, or a labelled phosphorylated ligand may be utilized.

The SH2 domain or subdomain thereof or phosphorylated ligand may be used to prepare monoclonal or polyclonal antibodies. Conventional methods can be used to prepare the antibodies. As to the details relating to the preparation of monoclonal antibodies reference can be made to Goding, J. W., Monoclonal Antibodies: Principles and Practice, 2nd Ed., Academic Press, London, 1986.

An SH2 domain or subdomain thereof or phosphorylated ligand may be labelled with various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive phosphorous $^{32}$P, iodine $I^{125}$, $I^{131}$ or tritium.

Radioactive labelled materials may be prepared by radiolabeling with $^{125}$I by the chloramine-T method (Greenwood et al. Biochem. J. 89:114, 1963), the lactoperoxidase method (Marchalonis et al. Biochem. J. 124:921, 1971), the Bolton-Hunter method (Bolton and Hunter, Biochem. J. 133:529, 1973 and Bolton Review 18, Amersham International Limited, Buckinghamshire, England, 1977), the iodogen method (Fraker and Speck. Biochem. Biophys. Res. Commun. 80:849, 1978), the Iodo-beads method (Marbell Anal. Biochem. 125:427, 1982) or with tritium by reductive methylation (Tack et al., J. Biol. Chem. 255:8842, 1980).

Known coupling methods (for example Wilson and Nakane, in "Immunofluorescence and Related Staining Techniques", W. Knapp et al, eds, p. 215, Elsevier/North-Holland, Amsterdam & New York, 1978; P. TiJssen and E. Kurstak, Anal. Biochem. 136:451, 1984) may be used to prepare enzyme labelled materials. Fluorescent labelled materials may be prepared by reacting the material with umbelliferone, fluorescein, fluorescein isothiocyanate, dichlorotriazinylamine fluorescein, dansyl chloride, derivatives of rhodamine such as tetramethyl rhodamine isothiocyanate, or phycoerythrin.

The SH2 domain or subdomain thereof or phosphorylated ligand used in the method of the invention may be insolubilized. For example, the SH2 domain or subdomain thereof or phosphorylated ligand may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The insolubilized SH2 domain or subdomain thereof or phosphorylated ligand may be prepared by reacting the material with a suitable insoluble carrier using known chemical or physical methods, for example, cyanogen bromide coupling.

The invention also provides a method for screening for antagonists that inhibit the affects of agonists of an SH2-phosphorylated ligand regulatory system. Thus, a substance that competes for the same binding site on the phosphorylated ligand or on the SH2-like domain or a subdomain thereof is screened for.

It will be understood that the substances that can be assayed using the methods of the invention may act on one or more of the SH2-binding site on the phosphorylated ligand or the ligand-binding site on the SH2-like domain or subdomain thereof, including agonist binding sites, competitive antagonist binding sites, noncompetitive antagonist binding sites or allosteric sites.

The invention also relates to a pharmaceutical composition comprising an isolated SH2-like domain or a subdomain thereof for use as an agonist or antagonist of the interaction of a signalling protein with a related phosphorylated ligand.

The pharmaceutical compositions of the invention contain an isolated SH2-like domain or a subdomain thereof alone or together with other active substances. Such pharmaceutical Compositions can be for oral, topical, rectal, parenteral, local, inhalant or intracerebral use. They are therefore in solid or semisolid form, for example pills, tablets, creams, gelatin capsules, capsules, suppositories, soft gelatin capsules, gels, membranes, tubelets.

The preparations of the invention can be intended for administration to humans or animals. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

On this basis, the pharmaceutical compositions include, albeit not exclusively, an isolated SH2-like domain or a subdomain thereof in association with one or more pharmaceutically acceptable vehicles or diluents, and contained in buffered solutions with a suitable pH and iso-osmotic with the physiological fluids.

The following non-limiting examples are illustrative of the present invention:

EXAMPLES

The following materials and methods were utilized in the investigations outlined in Examples 1 and 2:

Antibodies

Polyclonal rabbit antibodies against human GAP residues 171–448 or phosphotyrosine were raised and affinity-purified, as described in Ellis, C. et al Nature (London) 343, 377 (1990) and Kamps, M. P. & Sefton; B. M. Oncogene 2, 305 (1988). Anti-trpE rabbit antiserum was raised against a 37 Kda protein containing the N-terminal 323 residues encoded by the *Escherichia coli* trpE protein. Affinity-purified rabbit anti-phosphotyrosine antibodies were prepared as described in Kamps, M. P. & Sefton, B. M. Oncogene 2, 305 (1988). Antibodies directed against a peptide corresponding to residues 1176–1186 of the human EGF-R (Honegger, A. M. et al., Proc. Natl. Acad. Sci. 86, 925 (1989)) were utilized.

Cell Culture

Growth conditions, $^{32}$Pi labeling, EGF treatment, and immunoprecipitation of R1hER (obtained from M. Weber, University of Virginia, Charlottesville), Rat-2, and Rat-2 cells expressing v-src or v-fps genes were as described in Declue, J. & Martin, G. S. (1989) J. Virol. 63, 542–554; Koch, V. A. et al. (1989) Mol. Cell. Biol. 9, 4131–4140; and Ellis, C. et al (1990) Nature (London) 343,377–381.

Complex Formation with Bacterial trpE Fusion Proteins

Restriction fragments from human GAP, bovine PLC$_\gamma$ or v-crk CDNAS were subcloned into PATH bacterial TrpE expression vectors, using both natural and engineered restriction sites (Ellis, C. et al (1990) Nature (London) 343, 377–381). Fifty ml cultures of *E. coli* RR1 with the parental PATH expression plasmid, or a derivative encoding one of the various TrpE fusion proteins were grown and induced with indole acrylic acid as described in Moran, F. et al (1988) Oncogene 3, 665–672. Cells were washed with 1 ml of 50 mM Tris-HCl, pH 7.5, 10% (wt./vol.) sucrose followed by a 2 minute centrifugation at 15,000 x g. The cells were resuspended in 1 ml of ice-cold PLCLB (50 Mm HEPES, Ph 7.0/150 Mm NaCl/10% glycerol/1% Triton X-100/1.5 Mm $MgCl_2$/1 Mm EGTA/100 Mm NaF/10 Mm $NaPP_i$/1 Mm $Na_3VO_4$/I Mm phenyl/methylsulfonyl fluoride/aprotinin and leupeptin each at 10 µg/ml) sonicated 6 times for 10 seconds each and clarified by centrifugation at 15,000 x g for 15 minutes. Sonication and all subsequent steps were done at 4° C. Supernatants were incubated with 40 µl of anti-trpE serum and 30 µl of protein A-Sepharose beads. After being gently mixed for 90 minutes, the immune complexes were washed three times with HNTG buffer (20 Mm HEPES, Ph 7.0 150 Mm NaCl, 0.1% Triton X-100, 10% glycerol, 1 Mm $Na_3VO_4$) and divided into four equal aliquots. Similar amounts of the different TrpE fusion protein were detected in these immune complexes by immunoblotting with anti-TrpE antiserum.

For in vitro binding experiments, approximately $5 \times 10^6$ non-radioactive or $^{32}$P-labelled cells were lysed in 1 or 2 ml PLCLB and clarified as described below. One ml of clarified lysate was incubated with one aliquot of an anti-trpE immune complex. After mixing by gentle inversion for 90 minutes at 4° C., the immune complexes were recovered by centrifugation, washed three times with HNTG, resuspended in 40 µl of SDS sample buffer and heated at 100° C. for 3 minutes.

Immunoblotting

Cell lysates (prepared as in Koch, C. A. et al (1989) 9, 4131–4140; 25 µg of protein per lane), immunoprecipitates, and bacterial complexes were resolved by SDS-polyacrylamide gel electrophoresis and transferred to nitrocellulose in a semi-dry blotting apparatus at 0.8 Ma.cm$^{-2}$ for 60 minutes. Blots were analyzed by autoradiography ($^{32}$P-labelled samples) or were blocked and then probed with anti-EGFR antiserum (1:200 dilution) or antiphosphotyrosine antibodies as described in Koch, C. A. et al (1989) Mol. Cell. Biol. 9, 4131–4140. Antiphosphotyrosine blots of whole-cell lysates were probed with 10 µ Ci of $^{125}$I-labelled protein A (2–10 µ Ci/µg; 1 Ci=37 GBq; New England Nuclear), whereas all other blots were probed with 5 µ Ci of high-specific-activity $^{125}$I-labelled protein A (35 µ Ci/µg, Amersham). Blots were exposed to Kodak XAR film at –75° C. with an intensifying screen.

The following materials and methods were utilized in the investigations outlined in Examples 7 to 10:

Construction of bacterial expression vectors

A 415 bp HincII restriction fragment of murine c-fms cDNA encoding residues 646–784 was ligated in-frame into the bacterial expression plasmid pATH-2. Expression of this plasmid in *E. coli* yields a protein (WT TrpE-KI) in which TrpE is fused with a 139 amino acid fragment of the CSF-1R cytoplasmic domain containing the KI. Similar plasmids were constructed in which the HincII restriction fragments encoded a variety of Tyr-Phe mutations within the KI (F697, Phe697 mutant; F706, Phe706 mutant F721, Phe721 mutant; 2F, Phe697 and Phe706 double mutant; 3F, Phe697, Phe706 and Phe721 triple mutant). TrpE-COOH encodes a TrpE protein fused in-frame to amino acids 901–976 of the CSF-1R.

Sequences encoding the N-terminal (residues 312–444) or C-terminal (residues 612–722) SH2 domains of bovine p85α (Otsu et al., Cell 65, 91 (1991)) were amplified using the polymerase chain reaction (PCR) and cloned in-frame with the glutathione S-transferase (GST) sequences of plasmid pGEX2t to produce the constructs GEXp85αSH2N or GEXp85αSH2C, respectively. A larger PCR-amplified fragment encoding both SH2 domains (residues 312–722) was also ligated into the vector to generate GEXp85SH2N+C. Similarly, human GAP N-terminal SH2 sequences (amino acids 178–278 of human GAP) were cloned into pGEX2t to produce GEXgapSH2N.

Generation of bacterial clones co-expressing TrpE fusion proteins and the Elk tyrosine kinase

*Escherichia coli* containing various pATH expression plasmids were infected with a λ phage (λBI) encoding the cytoplasmic domain of the Elk tyrosine kinase as a LacZ-Elk fusion (Letwin et al., Oncogene 3, 621 (1988)). Infected bacteria were plated at 30° C. Single colonies were isolated and plated in duplicate at 30° and 42° C. Clones carrying the λB1 lysogen only grew at 30° C. and lysed at 42° C. The TrpE fusion proteins and the Elk tyrosine kinase were sequentially induced to achieve Elk-dependent tyrosine phosphorylation of TrpE fusion proteins. Following induction of TrpE fusion proteins at 30° C. as described above, the bacterial cultures were heat shocked at 42° C. followed by a 1 hour incubation with 1 mM isopropyl-β-D-thiogalactoside (IPTG) at 37° C. to induce the Elk kinase, and the consequent phosphorylation of the TrpE fusion proteins.

In vitro binding of TrpE-KI fusion proteins to PI 3'-kinase and to GST SH2 fusions Bacteria containing phosphorylated TrpE-KI from a 10 ml culture were pelleted and resuspended in 500 µl of PLC lysis buffer [50 mM N-2 hydroxyethylpiperazine-N-2-ethane sulfonic acid (HEPES), pH 7.5, 150 mM NaCl, 10% glycerol, 1% Triton X-100, 1.5 mM $MgCl_2$, 1 mM EGTA, 10 µg/µl aprotinin, 10 µg/µl leupeptin, 1 mM phenylmethylsulfonyl fluoride, 200 mM sodium orthovanadate, 10 mM pyrophosphate and 100 mM sodium fluoride]. The suspensions were sonicated and clarified by centrifugation. Clarified lysates were incubated for 90 minutes at 4° C. with rabbit anti-TrpE antibodies (1 µg/ml) and 100 µl protein A—Sepharose. Immunoprecipitates were washed three times with the lysis buffer and resuspended in a lysate from $2 \times 10^6$ Rat-2 cells and allowed to incubate for 60 minutes at 4° C. Rat-2 cells were lysed as described in Reedijk et al. (Mol. Cell. Biol. 10, 5601 (1990)). Immunoprecipitates were re-washed and analyzed for associated PI kinase activity as described in Fukui and Hanafusa, Mol. Cell. Biol. 9, 1651–1658 (1989). Aliquots of the immunoprecipitates were analyzed by immunoblotting with anti-TrpE or antiphosphotyrosine antibodies as described above.

GST fusion proteins containing p85α or GAP SH2 domains were induced with 1 mM IPTG. Bacterial lysates were prepared as above and the fusion proteins were immobilized with glutathione agarose beads. These immobilized SH2 domains were incubated with bacterial lysates containing TrpE-KI (or its various Tyr—Phe mutants) either in their phosphorylated or nonphosphorylated form. After 1.5 hours incubation at 4° C., the beads were washed and associated proteins were separated on a 12.5% polyacrylamide gel and transferred to nitrocellulose. Bound TrpE-KI fusion proteins were detected with anti-TrpE antibodies followed by[$^{125}$I] Protein A.

Phosphoamino acid analysis and two-dimensional tryptic phosphopeptide mapping

Following induction of TrpE-KI or TrpE-COOH fusion proteins at 30° C., bacterial cells from a 5 ml culture were pelleted and washed twice with phosphate-free Dulbecco's modified Eagle's medium. The washed cells were resuspended in 1 ml of the same medium and heat shocked at 42° C. for 15 minutes. 1 mCi of [$^{32}$P]orthophosphate was added to the medium followed by IPTG to a final concentration of 1 mM. After 1 hour incubation at 37° C. the cells were pelleted and washed with 50 mM Tris-HCl (pH 7.5), 0.5 mM EDTA, 0.3 M NaCl. The washed cells were lysed by incubation in 100 μl. SDS-cracking buffer (10 mM Na phosphate, pH7.5, 1% β-mercaptoethanol, 1% SDS, 6M urea) for 3 hours at 37° C. The lysate was diluted 20-fold with PLC buffer and clarified by centrifugation. $^{32}$P-Labelled TrpE-KI fusion proteins were isolated with anti-TrpE antibodies, separated by SDS-PAGE, and transferred to an Immobilon membrane. Immobilon strips containing the fusion proteins were excised, and the phosphoamino acid content of the $^{32}$P-labelled proteins were analyzed by acid hydrolysis, followed by two-dimensional electrophoresis at pH 1.9 and pH 3.5 (Cooper et al., Methods Enzymol, 99, 387–402 (1983)). For peptide mapping, $^{32}$P-labelled WT, F721, or 3F TrpE-KI proteins were immunoprecipitated with mouse monoclonal anti-TrpE antibodies bound to goat anti-mouse IgG agarose, and digested with trypsin. The full-length CSF-1R was immunoprecipitated from Rat-2 fibroblast cell line over-expressing c-fms with anti-Fms antiserum (Reedijk et al., Mol. Cell. Biol. 10, 5601–5608 (1990)), and autophosphorylated in vitro in the presence of [γ-$^{32}$P]ATP. Trypsin digestion of the full-length CSF-1R was performed on the nitrocellulose strip (Liu and Pawson, Mol. Cell. Biol. 11, 2511–2516 (1991)). All resulting peptides were separated by electrophoresis at pH 2.1, followed by ascending chromatography (Liu and Pawson, Mol. Cell. Biol. 11, 2511–2516 (1991)).

In vivo association of WT and mutant CSF-1R with PI 3'-kinase

WT and mutant CSF-1R cDNAs were cloned into an MuLV-based retroviral expression vector (Scharfmann et al., Proc. Natl. Acad. Sci. USA, 88, 4626–4630 (1991)). PA 12 packaging cells were transfected as described in van der Geer and Hunter, Mol. Cell. Biol., 11, 4698–4708 (1991). Supernatants were taken 48 hours after transfection and were used to infect 208F rat fibroblasts. Cells were selected for expression of the neomycin resistance gene in DMEM plus 400 μg/ml G418. Confluent 10 cm tissue culture dishes of 208F cells expressing WT and mutant CSF-1R cDNAs were starved in DMEM plus 10 mM HEPES, pH 7.4, and stimulated with 100 ng/ml rhCSF-1 for 3 minutes at 37° C. CSF-1R immunoprecipitates from control and CSF-1 stimulated cells were tested for PI 3'-kinase activity. Receptor immunoprecipitates obtained from parallel dishes were separated by SDS-PAGE, transferred to Immobilon P and probed for CSF-1R level as described before in van der Geer and Hunter, Mol. Cell. Biol., 11, 4698–4709 (1991).

Example 1

GAP and Crk SH2 Domains Bind a Related Set of phosphotyrosine-containing Proteins.

Figure 3:
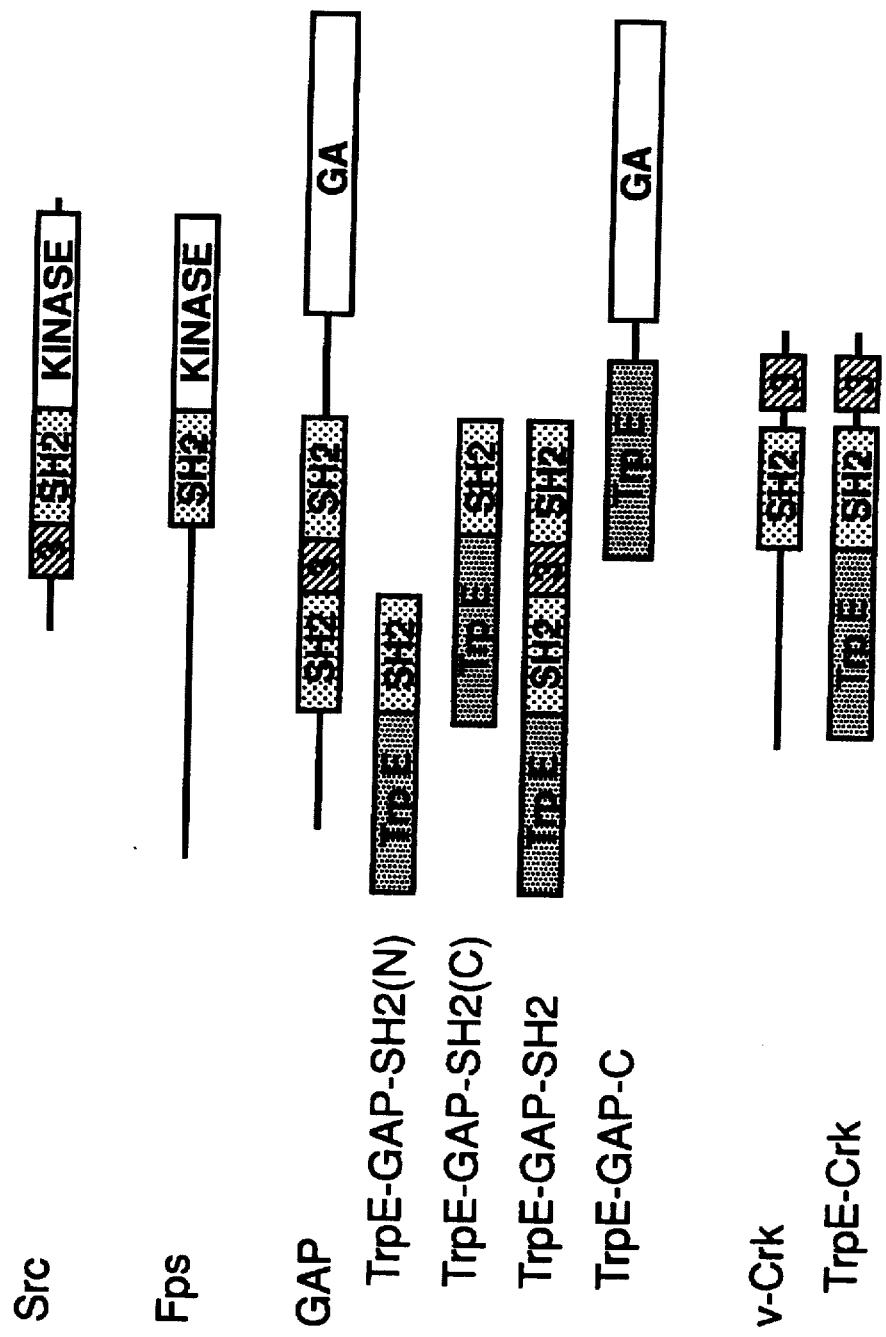
FIG. 3 shows the locations of SH2 and SH3 domains in signalling and transforming proteins and in TrpE fusion proteins.

The disposition of SH2 and SH3 domains within several signalling and transforming proteins is shown in FIG. 1. GAP was initially used to test whether these regions might be involved in protein-protein interactions. Different regions of GAP were expressed in bacteria as TrpE-GAP fusion proteins joined to a 37-Kda TrpE protein (FIG. 3). The fusion proteins contained the following residues: TrpE-GAP-SH2, human GAP 171–448; TrpE-GAP-SH2(N), GAP 178–278; TrpE-GAP-SH2(C), GAP 348–445; TrpE-GAP-C, GAP 670–1047; TrpE-V-Crk, P47$^{gag-crk}$ 206–327; TrpE-PLC$_γ$, bovine PLC$_γ$1 956–1291.3=SH3 domain; GA=GTPase activating region of GAP.

TrpE-GAP-SH2 contains almost precisely the two GAP SH2 domains and the intervening SH3 sequence. In contrast, TrpE-GAP-C contains the C-terminal half of GAP, including all residues required to stimulate p21$^{ras}$ GTPase activity (Marshall, M. S. et al (1989) EMBO. J. 8, 1105–1110). As controls, the TrpE protein by itself and a TrpE-PLC$_γ$ fusion protein containing C-terminal PLC$_γ$ catalytic sequences were used. These TrpE fusion proteins were immunoprecipitated with anti-TrpE antiserum.

To investigate whether these polypeptides could form specific complexes with proteins from src-transformed cells, the immunoprecipitates were incubated with a lysate of Rat-2 v-src cells (FIG. 4A Lanes 5–8) and with lysates of normal Rat-2 fibroblasts (FIG. 4A Lanes 1–4) and analyzed for associated proteins by immunoblotting with anti-phosphotyrosine antibodies. Phosphotyrosine bound to TrpE-GAP-SH2 from Rat-2 v-src cells (Lane 9) were also compared directly with an anti-GAP immunoprecipitate from the same lysate (Lane 10).

Figure 4A:
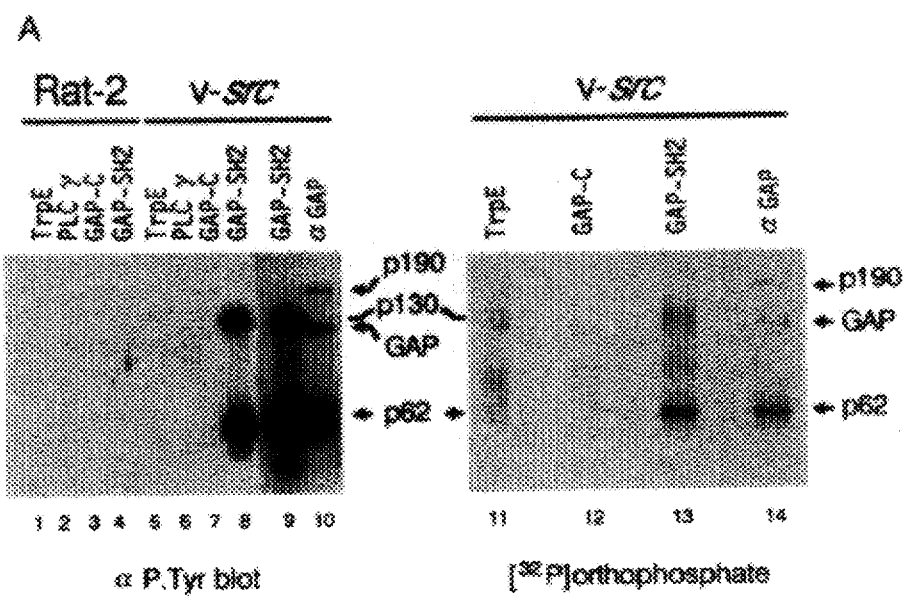
FIGS. 4A and 4B show the immunoblots and autoradiograms of TrpE fusion proteins that were mixed with lysates of normal Rat-2 cells or v-src transformed Rat-2 cells.

TrpE, TrpE-PLCγ and TrpE-GAP-C which lack SH2 sequences, did not retain any phosphotyrosine-containing proteins from the Rat-2 v-src lysate. However, TrpE-GAP-SH2 bound a 62 kDa tyrosine phosphorylated protein, as well as variable amounts of a 130 Kda protein (FIG. 4A). The 62 kDa protein co-migrated with p62 immunoprecipitated with anti-GAP antibodies from Rat-2 v-src cells.

As a more direct test of their binding activities, the TrpE fusion proteins were incubated with lysate of Rat-2 v-src cells that had been metabolically labelled with $^{32}$P$_i$ (Lanes 11–13). A lysate from $^{32}$P$_i$-labeled Rat-2 v-src cells was also incubated with anti-GAP antibodies (Lane 14). Precipitated $^{32}$P labelled proteins were visualized by autoradiography (right panel). Exposure time was 3 hours, except for lane 14 (18 hours). Again, TrpE-GAP-SH2 specifically bound a 62 kDa phosphoprotein that comigrated with GAP-associated p62 (FIG. 4A). The same result was obtained using $^{32}$P-labelled v-fps-transformed cells. Tryptic phosphopeptide analysis confirmed the identity of the 62-kDa SH2-binding protein as p62. p62 is not obviously related to p60$^{src}$, and lacks detectable in vitro protein kinase activity. The 130 Kda protein that bound the TrpE-GAP-SH2 may correspond to a protein (p130) whose phosphorylation by activated p60$^{src}$ requires the Src SH2 domain, with which it complexes in vivo (Reynolds, A. B. et al. (1989) Mol. Cell. Biol. 9, 3951–3958 and Lau, A. F. (1986) Virology 151, 86–99).

Figure 4B:
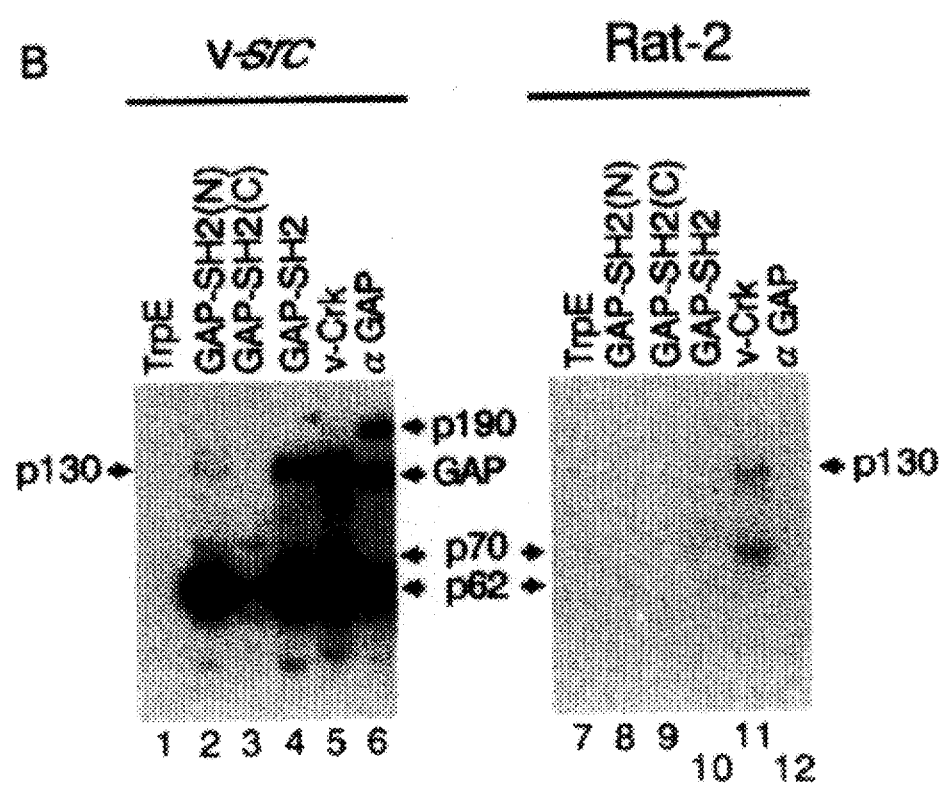

Immobilized TrpE (FIG. 4B), TrpE-GAP-SH2(N) (FIG. 4B), TrpE-GAP-SH2(C) (FIG. 4B), TrpE-GAP-SH2 (FIG. 4B) and TrpE-v-Crk (FIG. 4B) were incubated with lysates from Rat-2 v-src cells (FIG. 4B) or normal Rat-2 Cells (FIG. 4B). For comparison, anti-GAP immunoprecipitations (FIG. 4B) were made from the same cell lysates. Samples were analyzed by immunoblotting with anti-phosphotyrosine antibodies and $^{125}$I-Protein-A. Autoradiography was for 16 hours (lanes 1–6) or 3 days (lanes 7–14).

The binding sites for p62 and p 130 were more precisely ascribed to the N-terminal SH2 domain of GAP (GAP-SH2 (N), FIG. 3) which efficiently bound p62 and p130 from Rat-2 v-src cells (FIG. 4B).

To investigate whether these tyrosine phosphorylated proteins might be more general ligands for SH2-containing proteins similar experiments were done with a TrpE-v-Crk fusion protein (FIG. 3). TrpE-v-Crk also bound two phosphotyrosine-containing proteins when incubated with a Rat-2 v-src lysate, which likely correspond to p62 and p130 (FIG. 4B). TrpE-v-Crk bound p130 more efficiently than did TrpE-GAP-SH2, and also associated with a distinct 70 kDa tyrosine phosphorylated protein (p70). In lysates of normal Rat-2 cells TrpE-GAP-SH2 bound a small amount of p62, whereas TrpE-v-Crk formed more readily detectable complexes with p130 and p70 (FIG. 4B). It is of interest that phosphotyrosine-containing proteins of this size are associated with P47$^{gag\text{-}crk}$ in v-crk-transformed chicken embryo fibroblasts, and bind bacterial v-Crk in lysates of v-crk-transformed cells (Mayer, B. J. et al (1988) Nature (London) 332, 272–275; Mayer, B. J. et al (1988) (Cold Spring Harbor Symp. Quant. Biol. 53, 907–914; Mayer, B. J. & Hanafusa, H. (1990) Proc. Natl. Acad. Sci. U.S.A. 87, 2638–2642). These results indicate that the GAP and Crk SH2 domains have distinct but overlapping binding specificities. They bind common phosphotyrosine-containing ligands, but apparently with different efficiencies.

Example 2

The N terminal GAP SH2 Domain Binds Activated EGF Receptor In Vitro.

GAP has been implicated in the response to growth factors such as epidermal growth factor (EGF) and platelet-derived growth factor (PDGR), and shown to form a physical complex with the PDGF-receptor. Therefore the binding activity of TrpE-GAP bacterial proteins in lysates of Rat-1 cells expressing the human EGF-receptor (EGF-R)($\approx$2.5× 10$^5$ per cell) was investigated.

Figure 5A:
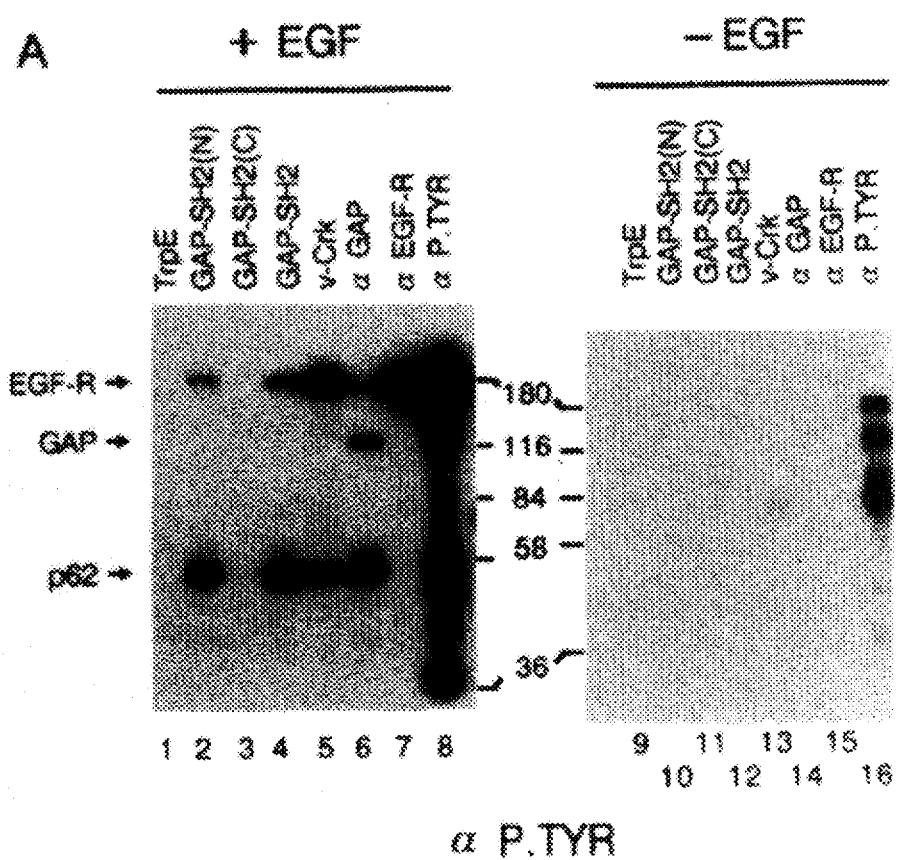
FIGS. 5A and 5B show the immunoblots of immobilized TrpE fusion proteins that were mixed with lysates of serum-starved Rat-1 cells overexpressing human EGFR that were stimulated with 0 or 80 nM EGF (A) and immunoblots with anti-EGFR antibodies of nitrocellulose filters containing duplicate samples of those in A (B)
Figure 5B:
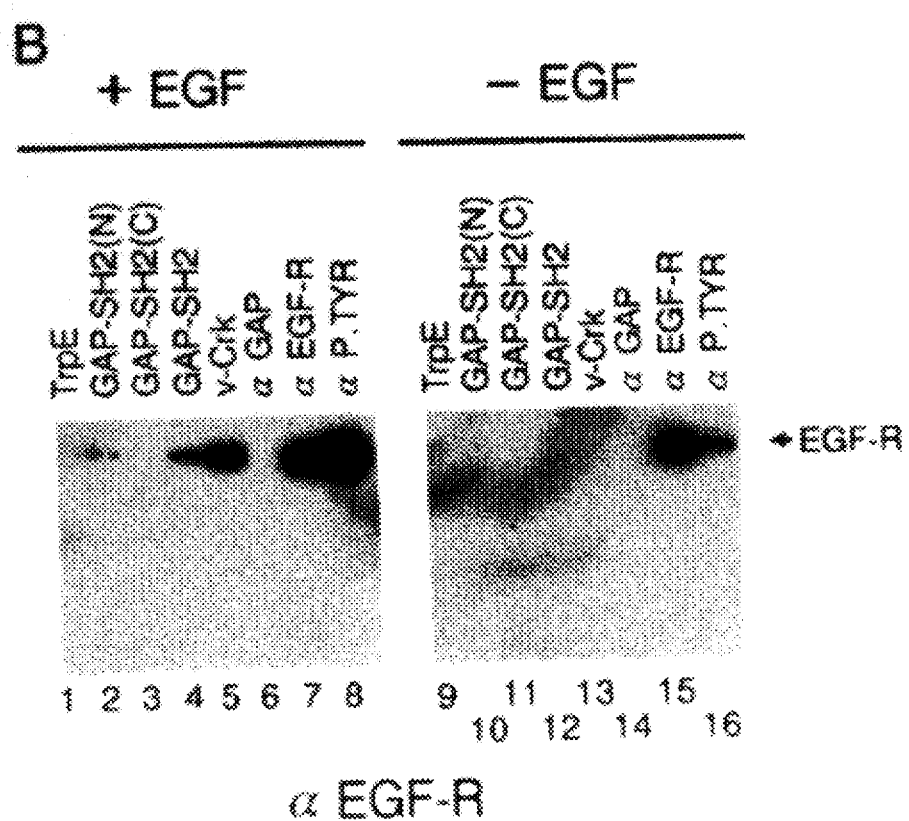

Serum-starved (for 48 hours) Rat-1 cells overexpressing human EGF-receptors were stimulated with 0 (FIG. 5 lanes 9 to 16), or with 80 nM EGF (lanes 1 to 8) for 5 minutes at 37° C. Cell lysates were mixed with the indicated TrpE bacterial fusion proteins, immobilized with anti-TrpE antibodies (lanes 1–5,9–13), or immunoprecipitated with anti-GAP (lanes 6,14), anti-EGF-R (lanes 7,15) or anti-phosphotryosine (lanes 8,16) antibodies. Complexes and immunoprecipitates were washed and analyzed by western blotting with antiphosphotryosine antibodies. Nitrocellulose filters containing duplicate samples of those describeed above were immunoblotted with anti-EGF-R antibodies (FIG. 5B).

No phosphotyrosine-containing proteins associated with immobilized TrpE fusion proteins before EGF stimulation (FIG. 5A), or with TrpE-GAP-C following addition of EGF. However, TrpE-GAP-SH2, TrpE-GAP-SH2(N) and TrpE-v-Crk precipitated two tyrosine phosphorylated proteins from lysates of EGF-stimulated cells, with mobilities of 62 and 180 kDa (FIG. 5A). The 62 kDa protein comigrated with p62 precipitated from the EGF-stimulated lysate with anti-GAP antibodies. The 180 kDa band comigrated with the EGF-R immunoprecipitated from the same lysate, was recognized by anti-EGF-R antibodies on an immunoblot (FIG. 5B), and was phosphorylated on tyrosine in an in vitro kinase reaction. These data show that the 180-kDa protein is the EGF-R and that its association with SH2 domains is clearly dependent on prior EGF stimulation (FIG. 5B). TrpE-v-Crk bound the EGF-R more effectively than the GAP SH2 fusion proteins, but was less efficient in p62-binding (FIGS. 5A and B, lane 5)

Example 3

Figure 6A:
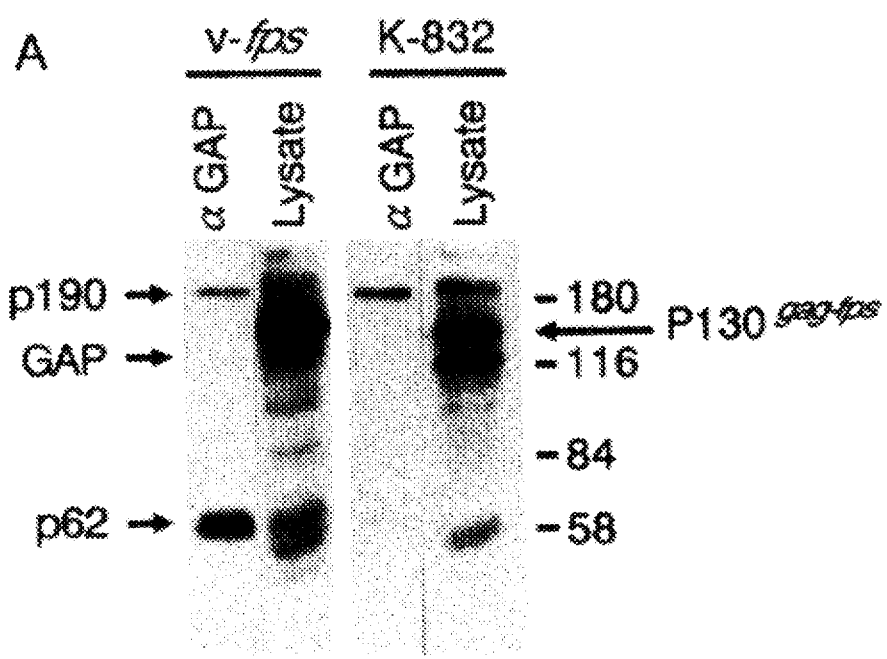
FIGS. 6A and 6B show immunoblots with anti-phosphotyrosine antibodies of total cell lysates, or anti-GAP immunoprecipitates from Rat-2 cells expressing either wild type $P130^{gag\text{-}fps}$ (v-fps), or mutant $P130^{gag\text{-}fps}$ with a glu$^{832}$->lys amino acid substitution in the SH2 domain (K-832) (A) and immunoblots with anti-phosphotyrosine antibodies of anti-GAP immunoprecipitates, or total cell lysates from Rat-2 cells expressing wild type v-src, or the SRX5, SHX13 or XD6 v-src mutants, or containing empty vector.

Fps and Src SH2 Domains Are Required for Tyrosine Phosphorylation of p62 and GAP.

p62 is rapidly and abundantly phosphorylated by activated v-Src and v-Fps tyrosine kinases (Ellis, C., et al. (1990) Nature (London) 343, 377–381). The v-Fps SH2 domain, and Glu-832 in particular have been previously implicated in recognition of a 62-kDa protein whose phosphorylation correlates with transformation (Koch, C. A. et al. (1989) Mol. Cell. Biol. 9, 4131–4140). Therefore, an investigation was carried out to determine whether this substrate corresponds to p62, which displays an affinity for SH2 domains in vitro (see Example 1). In particular, total cell lysates, or anti-GAP immunoprecipitates from Rat-2 cells expressing either wild type P130$^{gag\text{-}fps}$ (v-fps), or a glu$^{832}$->lys amino acid mutant (K-832) were analyzed by immunoblotting with anti-phosphotryosine antibodies. Direct comparison revealed that GAP-associated p62, precipitated with anti-GAP antibodies from cells transformed by wild type (wt) v-fps, comigrated with the prominent SH2-dependent 62-kDa substrate identified in the whole cell lysate. Furthermore, little phosphotyrosine-containing p62 could be detected in anti-GAP immunoprecipitates from cells expressing a v-Fps mutant with a substitution of lysine for Glu-832 in the SH2 domain (FIG. 6A). GAP itself is a relatively poor substrate for P130$^{gag\text{-}Fps}$ (Ellis, C. et al. (1990) Nature (London) 343, 377–381); prolonged exposure revealed that GAP tyrosine phosphorylation also depends on the v-Fps SH2 domain.

A series of in-phase linker-insertion and deletion mutations constructed in v-src has yielded several mutants that have relatively high levels of p60$^{v\text{-}src}$ kinase activity, but are poorly transforming in Rat-2 cells (DeClue, J. & Martin, G. S. (1989) J. Virol. 63, 542–554). The XD6 and SHX13 mutants have alterations within highly conserved regions of the v-Src SH2 domain. XD6 has a deletion of residues 149–174, and the SHX 13 mutation inserts Arg-Ala after residue 228. In contrast, the SRX5 mutation replaces the codon for the tyr$^{416}$ autophosphorylation site in the catalytic domain with codons for Ser-Arg-Asp.

Figure 6B:
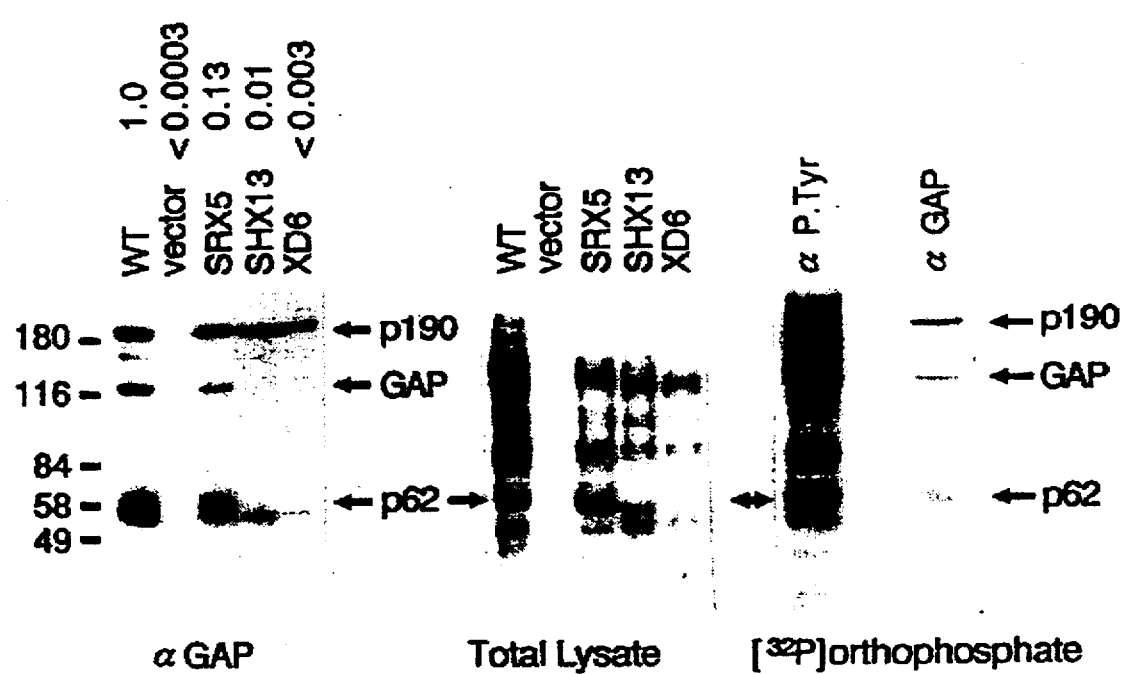

Anti-GAP immunoprecipitates (FIG. 6B, left panel), or total cell lysates (FIG. 6B, middle panel) from Rat-2 cells expressing wild type v-src, or the SRX5, SHX13 or XD6 v-src mutants, or containing empty vector, were analyzed by immunoblotting with anti-phosphotyrosine antibodies. The focus forming activities of the v-src mutants on Rat-2 cells relative to wt are indicated (DeClue, J. & Martin, G. S. (1989) J. Virol. 63, 542–554). In addition, Rat-2 v-src cells were metabolically labelled with $^{32}$Pi for 2 hours, followed by immunoprecipitation with anti-phosphotyrosine or anti-GAP antibodies. These immunoprecipitates were separated by gel electrophoresis, transferred to immunoblots and subjected to autoradiography (FIG. 6B, right panel).

Rat-2 cells expressing these v-src mutants contained similar levels of GAP and p60$^{v\text{-}src}$ compared with wild type v-src-transformed cells. However, anti-GAP immunoprecipitations showed that the tyrosine phosphorylation of GAP-associated p62, and of GAP itself, was greatly decreased in cells expressing the SHX13 and XD6 v-src SH2 mutants, correlating with their particularly low Rat-2 transforming activity (FIG. 6B). In contrast, the SRX5 autophosphorylation site mutant has an intact SH2 domain, retains 13% of wild type transforming activity on Rat-2 cells, and still gives appreciable phosphorylation of p62 and GAP. Unlike p62, which is minor but highly phosphorylated protein, p190 contains relatively little phosphotyrosine but it is a major GAP-binding protein (Ellis, C. et al (1990) Nature (London) 343,377–381). p190 tyrosine phosphorylation was not affected by the v-src or v-Fps SH2 mutations and hence, does not require the tyrosine kinase SH2 domain and does not correlate with transformation. Binding of tyrosine phosphorylated p190 to GAP SH2 domains or C-terminal region in vitro was not observed, possibly because all the available p190 is already associated with GAP in cell lysates.

Example 4

SH2 domains of PLCγ1 synthesized in bacteria bind synergistically in vitro to activated EGF- and PDGF-receptors.

The following materials and methods were utilized in the example:

Restriction sites were introduced on either side of SH2 coding sequences in the cDNA's for bovine PLCγ1 and human GAP with oligonucleotide-directed mutagenesis (Kunkel, et al., Methods Enzymol. 154, 367 (1987)). For each individual SH2 domain an Sph I site was created at the 5' end and an Nhe I site at the 3' end. These Sph INhe I fragments were cloned into a pATH bacterial trpE expression vector whose multiple cloning site had been modified to contain unique Sph I and Nhe I sites. For fusions that contained both SH2 domains, the Sph I site of the NH$_2$-terminal SH2 domain and the Nhe I site of the COOH-terminal SH2 domain were used for the excision. Src and Crk fusion proteins utilized natural restriction sites. The resulting fusion proteins contained the NH$_2$- terminal 323 amino acids of TrpE and retained the desired reading frame for PLCγ1 or GAP.

Cultures of *E. coli* RR1 with pATH expression plasmids were grown, induced, and lysed as described above in Example 1. The TrpE fusion proteins were recovered from the supernatants by immunoprecipitation with polyclonal anti-TrpE antiserum immobilized on protein A-Sepharose beads. Immune complexes were washed, aliquoted, flash-frozen, and stored at −70° C. until mixed with mammalian cell lysates. Starved or growth factor-stimulated rat fibroblasts (~5×10$^6$) were lysed in 2 ml of lysis buffer (50 mM Hepes, pH 7.0, 150 mM NaCl, 10% glycerol, 1% Triton X-100, 1.5 mM MgCl$_2$, 1 mM EGTA, 100 mM NaF, 10 mM sodium pyrophosphate, 1 mM Na$_3$VO$_4$, 1 mM PMSF, 10 µg/ml aprotinin, 10 µg/ml leupeptin). Clarified mammalian cell lysate (1 ml) was mixed with immobilized bacterial fusion protein by gentle inversion for 90 min at 4° C. Complexes were recovered by centrifugation, washed three times with HNTG buffer (20 mM Hepes pH 7.0, 150 mM NaCl, 0.1% Triton X-100, 10% glycerol, 1 mM Na$_3$VO$_4$), and analyzed by immunoblotting with anti-P.Tyr or anti-receptor as described in Kazlauskas et al. Science 247, 1578 (1990); Koch et al. Mol. Cell. Biol. 9, 4131 (1989); and Ellis et al., Nature 343, 377 (1990). To ensure that the different TrpE fusion proteins were present in similar amounts in the immune complexes incubated with the mammalian cell lysates, duplicate samples for anti-P.Tyr and anti-EGF-R immunoblotting were probed with an anti-TrpE monoclonal antibody. Equivalent amounts of the various TrpE fusion proteins were detected.

To investigate the possibility that enzymes such as PLC$_γ$ and GAP associate directly with activated tyrosine kinase receptors by virtue of their SH2 domains, restriction sites were introduced into the complementary DNA (cDNA) for bovine PLCγ1, which allowed the precise excision of the NH$_2$- terminal and COOH-terminal SH2 domains (SH2[N] and SH2[C]), either alone or together (See detailed method described above and FIG. 7). The individual SH2 domains, or the two SH2 domains together (SH2[N+C]) were introduced into a bacterial expression vector (pATH) and expressed as TrpE fusion proteins in *Escherichia coli*. These proteins were isolated from bacterial lysates by immunoprecipitation with antibodies to TrpE (anti-TrpE) attached to Sepharose beads (See detailed method described above).

Figure 8:
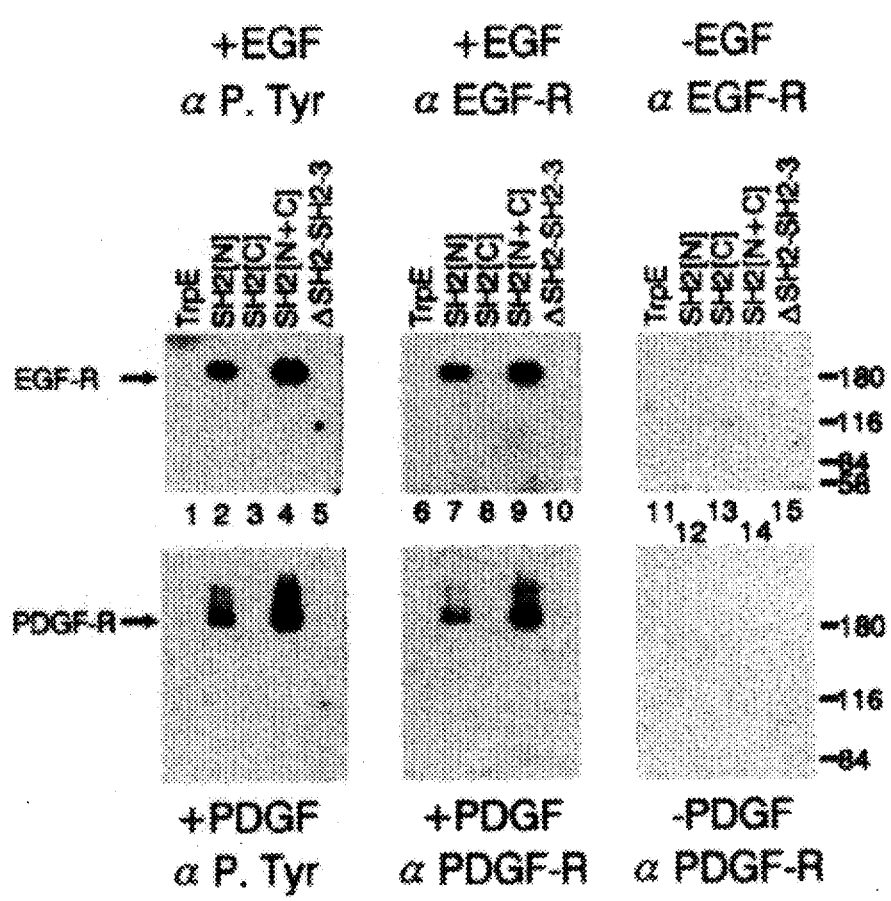
FIG. 8 shows immunoblots of immobilized TrpE fusion proteins that were mixed with lysates of Rat-1 cells overexpressing EGFR (A) and lysates from serum-starved Rat-2 cells stimulated with 75 nMBB-PDGF (B)

The immobilized bacterial proteins (parental TrpE or the indicated TrpE-PLCγ1 bacterial fusion proteins) were incubated with lysates of Rat-1 cells that overexpressed the human EGF-R (R1hER), which had been serum-starved for 48 hours (FIG. 8, lanes 11 to 15) or stimulated for 5 min at 37° C. with 80 nM EGF (FIG. 8, lanes 1 to 10). Complexes were washed, resolved on 8.25% SDS-polyacrylamide gels, and analyzed by immunoblotting with either anti(α)-P.Tyr (FIG. 8, lanes 1 to 5) or anti-EGF-R (FIG. 8, lanes 6 to 15) followed by I$^{125}$-labelled protein A. Autoradiography was for 18 hours. Immobilized TrpE or TrpE-PLCγ1 fusion proteins were also incubated with lysates from Rat-2 cells that were serum-starved for 48 hours (FIG. 8, lanes 11 to 15) or stimulated for 5 min at 37° C. with 75 nMBB-PDGF (FIG. 8, lanes 1 to 10). Samples were resolved on 6% SDS-polyacrylamide gels and analyzed by immunoblotting with either anti-P.Tyr (FIG. 8, lanes 1 to 5) or anti-PDGF-R (FIG. 8, lanes 6 to 15).

The TrpE-PLC-SH2[N] fusion protein complexed specifically with a 180-kilodalton (kD) P.Tyr-containing protein in lysates of EGF-stimulated cells. Immunoblotting of duplicate samples with antibodies to the EGF-R confirmed that this protein was the EGF-R and showed that its in vitro association with the PLCγ1 SH2[N] domain was EGF-dependent (FIG. 8). The PLCγ1 SH2[N] domain was more efficient than the SH2[C] domain in its ability to bind the EGF-R. Interestingly, the fusion protein that contained both NH$_2$- and COOH-terminal SH2 domains bound two to four-fold more EGF-R in EGF-stimulated cell lysates than could be accounted for by the two individual SH2 domains. The PLCγ1 SH2 domains therefore functioned synergistically in binding to the activated EGF-R. Very similar results were obtained for interactions of the PLCγ1 SH2 domains with the PDGF-R (FIG. 8). The PLCγ1 SH2[N] domain bound the PDGF-R in lysates of cells treated with the BB homodimeric form of PDGF but not in lysates of unstimulated cells. As observed for the EGF-R, the PLCγ1 SH2[C] domain alone was inefficient in binding activated PDGF-R, but bound synergistically with the SH2[N] domain when both domains were expressed as one bacterial protein (FIG. 8).

Within the SH2 domain, there are motifs that are particularly highly conserved. For example the NH$_2$- terminal tryptophan is invariant, and most SH2 domains start with the consensus W(Y.F)(H.F)GK (Koch et al. Mol. Cell. Biol. 9, 4131 (1989)). (Note Abbreviations for the amino acid residues are: A, Ala; C, Cys; D, Asp; E, Glu; F, Phe; G, Gly; H, His; I, Ile; K, Lys; L, Leu; M, Met; N, Ash; P, Pro; Q, Gln; R, Arg; S, Ser; T, Thr; V, Val; W, Trp; and Y, Tyr.) These residues may have been conserved because they are important in the interactions of SH2-containing proteins with activated growth factor receptors. A TrpE fusion protein that contained both PLCγ1 SH2 domains, with the exception that the first four residues of SH2[N] (W-F-H-G) were deleted (PLC SH2-SH2-3) was expressed and its association with phosphotyrosine containing proteins in cell lysates using the techniques described above was investigated. The fusion protein showed a modest ability to bind activated EGF- or PDGF-R (FIG. 8, lanes 5 and 10) that was equivalent to the SH2[C] domain alone, indicating that the removal of the four residues weakened binding activity.

Example 5

Binding of TrpE fusion proteins that contain the GAP Src, or Crk SH2 domains to PDGF-R in lysates of PDGF-stimulated Rat-2 cells.

The following procedure was used to investigate binding of TrpE fusion proteins that contain GAP, Src, or Crk SH2 domains to PDGF-R in lysates of stimulated Rat-2 cells. Serum- starved Rat-2 cells were stimulated for 5 min at 37° C. with 75 nM BB-PDGF, lysed, and mixed with the indicated immobilized TrpE bacterial fusion proteins. Complexes were washed, resolved on 7.5% SDS-polyacrylamide gels and analyzed by immunoblotting with anti-P.Tyr (8 hour exposure) or with anti-PDGF-R (18 hour exposure).

Figure 7:
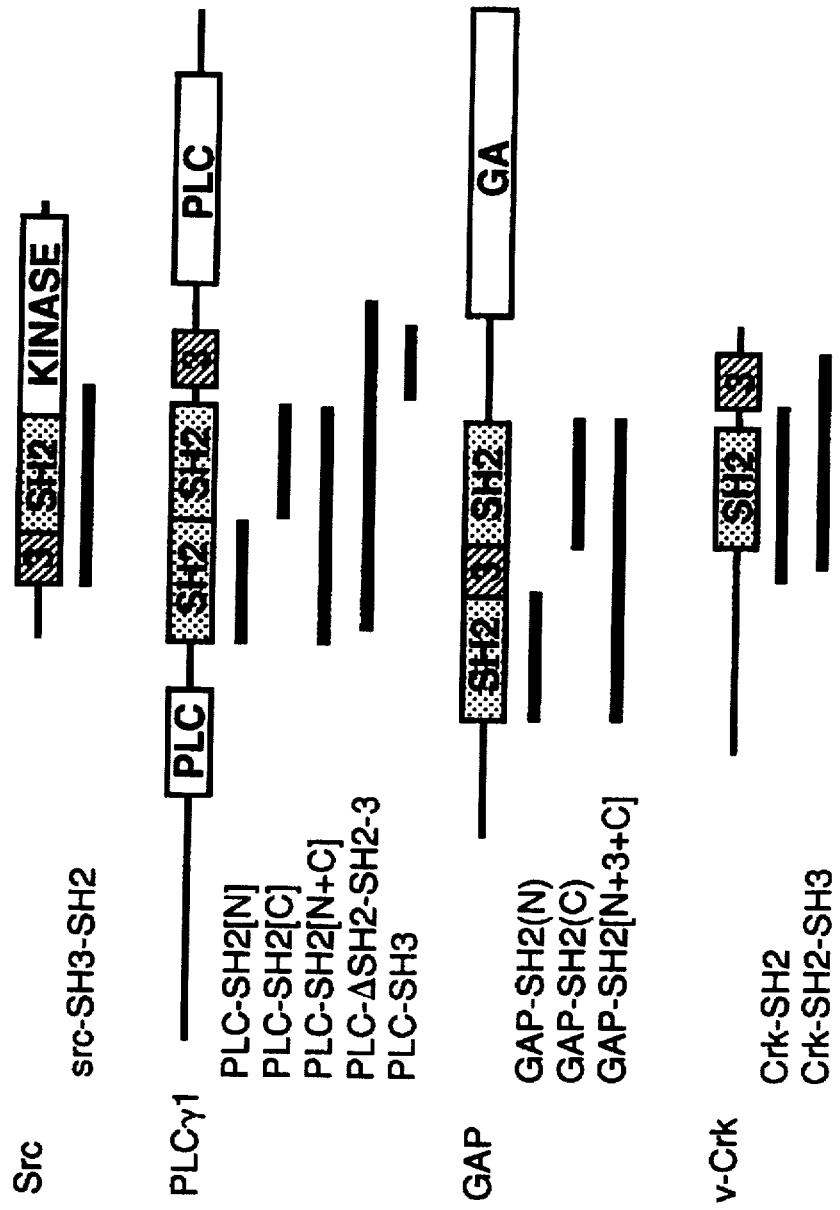
FIG. 7 shows the locations of SH2 and SH3 domains in TrpE fusion proteins.
Figure 9:
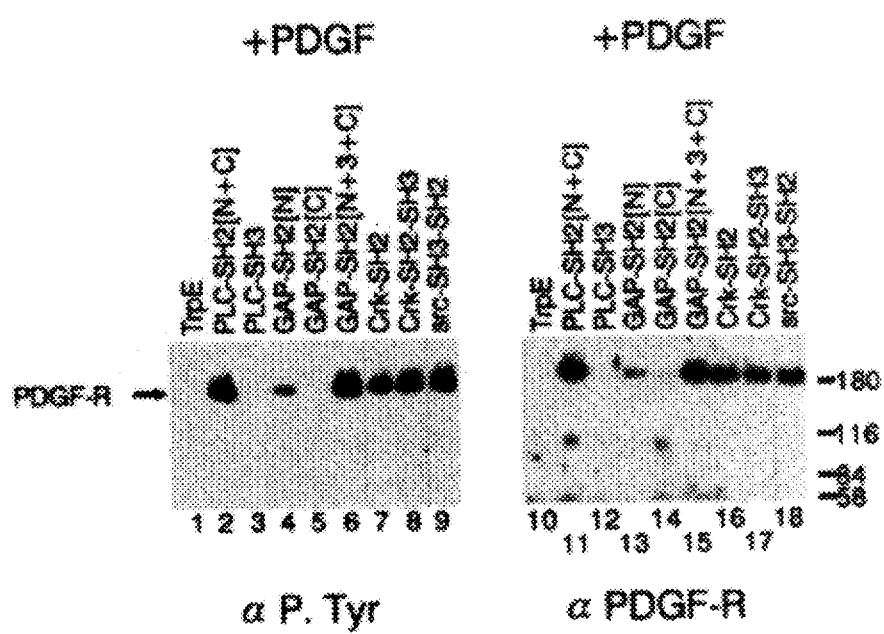
FIG. 9 shows immunoblots of immobilized TrpE fusion proteins that were mixed with serum-starved Rat-2 cells stimulated with 75 nM BB-PDGF.

Because GAP also associates with the PDGF-R, experiments were carried out using bacterial GAP SH2 sequences (see FIG. 7). The GAP SH2 [N] domain bound the PDGF-R in a lysate of PDGF-stimulated cells (FIG. 9), but not in unstimulated cells. The GAP SH2[C] domain exhibited much weaker PDGF-R-binding activity. However, the two SH2 domains together (GAP-SH2[N+3+C] bound the receptor threefold more efficiently than expected from their individual binding activities (FIG. 9, lanes 4 to 6 and 13 to 15). GAP contains an SH3 domain, which intervenes between the two SH2 elements and might contribute to binding to receptors. This seems unlikely, because the PLC$\gamma$1 SH3 domain, expressed in isolation as a TrpE fusion protein, did not associate with the PDGF-R (FIG. 9).

Src-like tyrosine kinases and v-Crk also contain SH2 domains, which may bind activated receptors. Consistent with this prediction, bacterial fusion proteins that contained the SH2 domains of p60$^{src}$ or P47$^{gag-crk}$ bound PDGF-R in lysates of PDGF-stimulated Rat-2 cells (FIG. 9). p60$^{src}$ is a substrate for the PDGF-R (Ralston and Bishop, Proc. Natl. Acad. Sci. U.S.A. 82, 7845 (1985); Gould and Hunter, Mol. Cell. Biol. 8, 3345 (1988)), and recent evidence suggests that Src-like kinases are physically associated with activated PDGF-R in vivo (Kypta et al. Cell 62, 481 (1990)). The data herein imply that this interaction involves the Src SH2 domain. Whether the normal homolog of v-Crk complexes with growth factor receptors in vivo remains to be established.

Example 6

Inhibition of in vitro binding of both PLC$\gamma$1 and GAP SH2 domains to the activated PDGF-R in Rat-2 cells that overexpress PLC$\gamma$1.

Only a minor fraction of activated PDGF-R complexes with PLC$\gamma$1 in vivo. A Rat-2 cell line was genetically modified to overexpress PLC$\gamma$1 by tenfold as compared with the endogenous enzyme (Rat-2 PLC$\gamma$1). There is a proportionate increase in the amount of PDGF-R precipitated with antibodies to PLC$\gamma$1 (anti-PLC$\gamma$1) after PDGF stimulation of Rat-2 PLC$\gamma$1 cells, in comparison with parental Rat-2 cells. If bacterial PLC$\gamma$1 SH2 domains bound to the same site(s) on the PDGF-R as did cellular PLC$\gamma$1, then overexpression of PLC$\gamma$1 should block binding of bacterial PLC$\gamma$1 SH2 domains to activated PDGF-R in vitro. To investigate this Rat-2 cells (FIG. 10, lanes 1, 2, 5 and 6) or a Rat-2 cell line that overexpressed PLC$\gamma$1 by tenfold (R2-PLC$\gamma$; lanes 3, 4, 7, 8) were stimulated with PDGF (lanes 1, 3, and 5–8) or maintained without PDGF (lanes 2 and 4). Cell lysates were mixed with immobilized TrpE-PLC-SH2[N] (lanes 1 to 4), TrpE-PLC-SH2[N+C] (lanes 5 and 7), or TrpE-GAP-SH2 [N+3+C] (lanes 6 to 8). Samples were washed, separated by gel electrophoresis, and immunoblotted with anti-P.Tyr. Similar results were obtained by blotting with anti-PDGF-R.

Figure 10:
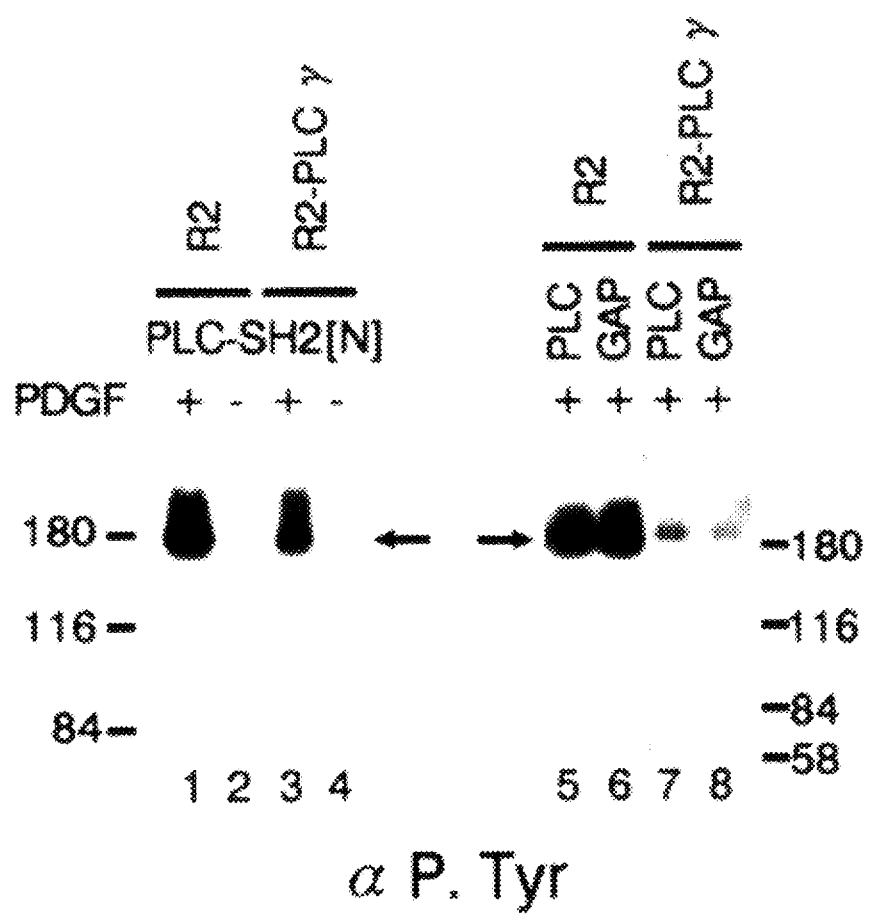
FIG. 10 shows immunoblots of immobilized TrpE fusion proteins mixed with Rat-2 cells that overexpress PLCγ1.

When the Rat-2 PLC$\gamma$1 cell line was stimulated with PDGF, lysed, and incubated with immobilized PLC$\gamma$1-SH2 [N] or PLC$\gamma$1 SH2[N+C], only one-third as much PDGF-R associated with the bacterial protein, compared with the parental PDGF-stimulated Rat-2 cells (FIG. 10). Binding of TrpE-GAP-SH2 fusion protein to the PDGF-R was also reduced by overexpression of endogenous PLC$\gamma$1, suggesting that PLC$\gamma$1 and GAP compete for sites on the activated PDGF-R.

Example 7

Phosphorylation-dependent binding of the isolated CSF-1R KI to PI 3'-kinase.

Figure 11:
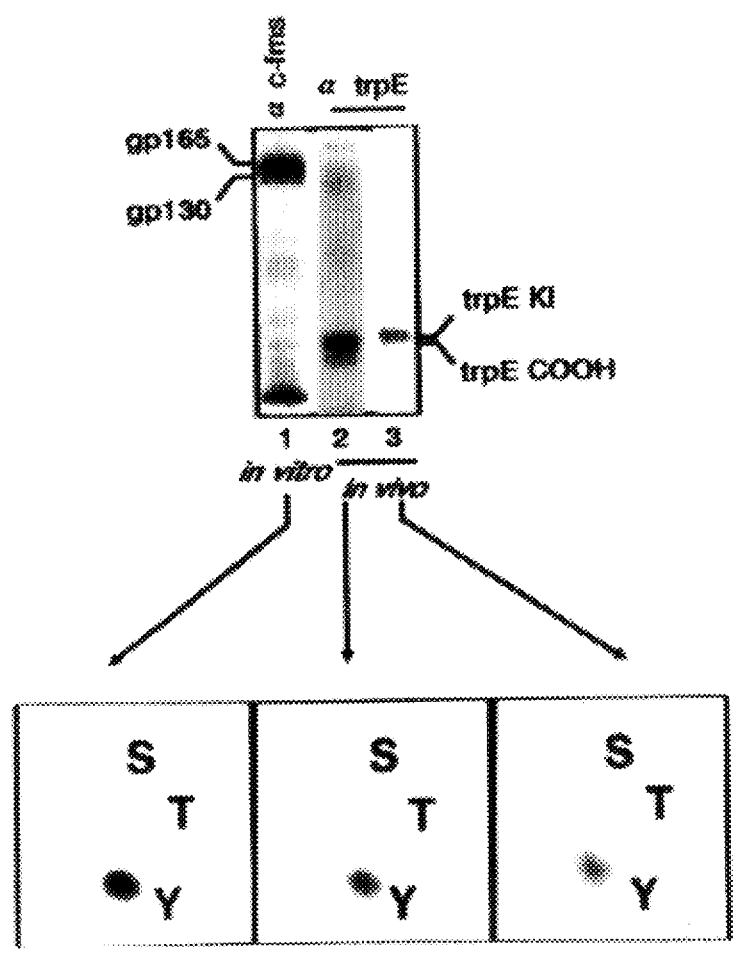
FIG. 11 shows immunoblots with anti-TrpE antibodies of phosphorylated TrpE-fusion proteins (A) and the results of phosphoamino acid analysis of the TrpE-fusion proteins.

To investigate the binding properties of the CSF-1R KI, the domain of the receptor was expressed in bacteria, and its ability to bind PI 3'-kinase was assessed. For this purpose a sequence encoding 139 residues of the mouse CSF-1R, which includes the entire KI, was excised from the c-fms cDNA (Rothwell and Rohrschreider, Oncogene 1, 311–324 (1987)) and expressed as a TrpE fusion protein in *Escherichia coli* (TrpE-KI). To induce tyrosine phosphorylation of the TrpE-KI fusion protein, bacteria harboring the TrpE-KI plasmid were infected with a $\lambda$gt11 bacteriophage ($\lambda$B1-Elk) encoding the cytoplasmic domain of the Elk tyrosine kinase, which is extremely active in *E. coli* (Letwin et al., Oncogene 3, 621–627 (1988)). Bacteria containing the TrpE-KI plasmid and the $\lambda$B1-Elk bacteriophage as a lysogen were isolated. The *E. coli* were labelled with [$^{32}$P]orthophosphate, and the TrpE fusion protein and the Elk tyrosine kinase were sequentially induced. Labelled bacterial lysates were immunoprecipitated with anti-TrpE antibodies ($\alpha$TrpE), and the immune complexes were separated by polyacrylamide gel electrophoresis, transferred to an Immobilon membrane, and subjected to autoradiography (FIG. 11 A TrpE-KI, lane 3).

WT mouse CSF-1R (gp165, gp130) was immunoprecipitated from Rat-2 cells expressing c-fms with anti-Fms antibodies, and autophosphorylated in vitro using [$\gamma$-$^{32}$P] ATP (FIG. 11A lane-1). $^{32}$P-Labelled CSF-1R and TrpE-KI were excised from the membrane and were analyzed for phosphoamino acid content. The positions of unlabelled phosphoamino acid markers are shown: phosphoserine (S); phosphothreonine (T) and phosphotyrosine (Y). As shown in FIG. 11A, the TrpE-KI fusion protein became phosphorylated (FIG. 11A, lane 3). Phosphoamino acid analysis of the TrpE-KI protein immunoprecipitated from $^{32}$P-labelled *E. coli* expressing the Elk tyrosine kinase revealed phosphotyrosine as the only detectable phosphoamino acid (FIG. 11B).

Figure 12:
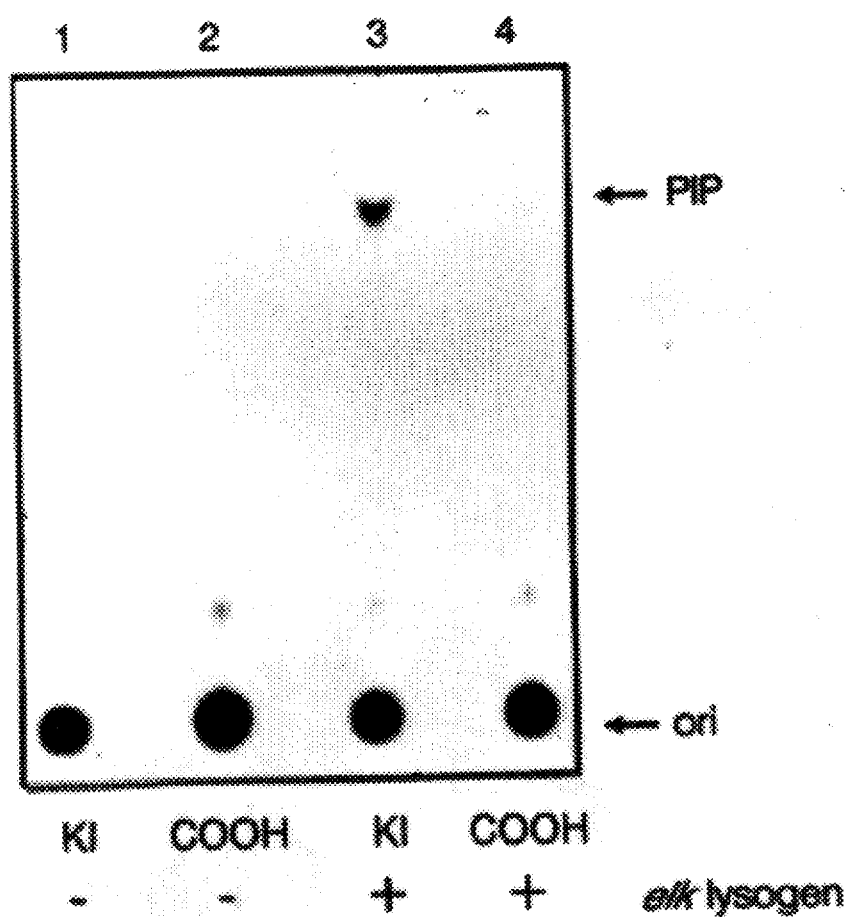
FIG. 12 shows immunoblots of immobilized TrpE fusion proteins mixed with Rat-2 cells that express PI 3'-kinase.

To test for PI 3'-kinase binding activity, the unphosphorylated or tyrosine phosphorylated TrpE-KI fusion proteins were isolated by immunoprecipitation of unlabelled bacterial extracts, incubated with lysates of Rat-2 fibroblasts, washed and assayed for associated PI 3'-kinase activity (FIG. 12). In particular, either non-phosphorylated (–elk lysogen, lanes 1 and 2) or tyrosine phosphorylated (+elk lysogen, lanes 3 and 4) TrpE fusion proteins (TrpE-KI, lanes 1 and 3; TrpE-COOH, lanes 2 and 4) were isolated from bacterial lysates with anti-TrpE antibodies, and immobilized on protein A—Sepharose beads. 2×10$^6$ Rat-2 cells were lysed as described in Reedijk et al., Mol. Cell. Biol. 10, 5601–5608, 1990, and incubated with the immobilized TrpE fusion proteins for 1 hour at 4° C. Complexes were then washed, and tested for associated PI 3'-kinase activity. (ori, origin. PIP, phosphatidylinositol monophosphate) As shown in FIG. 12 the unphosphorylated TrpE-KI protein showed no binding activity. In contrast the tyrosine phosphorylated TrpE-KI bound PI 3'-kinase activity when incubated with a Rat-2 cell lysate.

To investigate whether PI 3'-kinase binding is a specific property of the KI, a 76 amino acid C-terminal fragment of the CSF-1R was also expressed in *E. coli* as a TrpE fusion protein (TrpE-COOH). When the TrpE-COOH protein was co-expressed with the $\lambda$B1-Elk tyrosine kinase it became extensively tyrosine phosphorylated, albeit at sites which may be non-physiological (FIG. 11A TrpE-COOH, lane 2). However, neither the unphosphorylated nor the tyrosine phosphorylated TrpE-COOH proteins were able to bind PI 3'-kinase in a Rat-2 cell lysate (FIG. 12). Hence PI 3'-kinase binding requires tyrosine phosphorylation within a specific context provided by the KI.

Example 8

Binding of PI 3'-kinase to bacterially expressed KI requires phosphorylation of CSF-1R Tyr721.

Figure 13:
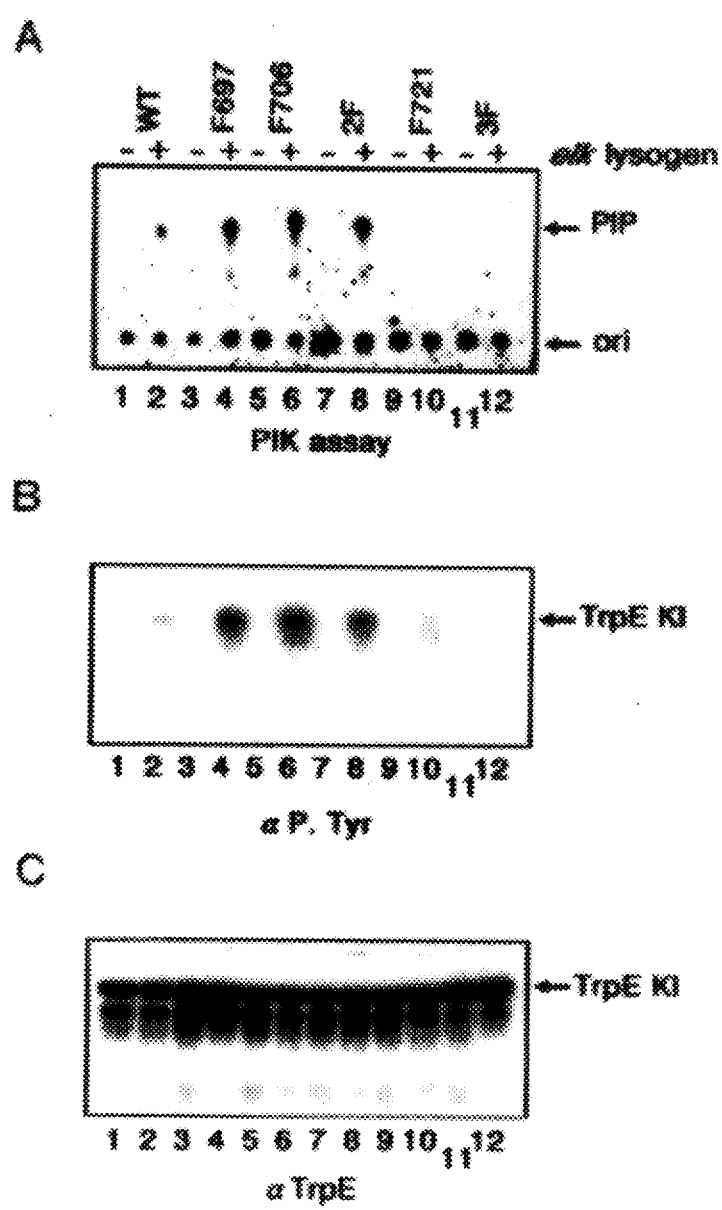
FIGS. 13A–13C show immunoblots of immobilized TrpE-KI fusion proteins containing tyrosine to phenylalanine mutations at various locations within the KI fusion proteins mixed with Rat-2 cells that express PI 3'-kinase (A); and, Western blotting analysis with antiphosphotyrosine antibodies (b) or anti-TrpE antbodies (C)

The identity of the tyrosine residue(s) necessary for association of the CSF-1R KI with PI 3'-kinase was addressed by substituting each of the three tyrosine residues in the KI, Tyr697, Tyr706 and Tyr721, with phenylalanine (Phe) in the TrpE-KI fusion protein. The mutant proteins were expressed in E. coli with λB1-Elk tyrosine kinase, and analyzed for their tyrosine phosphorylation and PI 3'-kinase binding activity (FIG. 13). Specifically, TrpE-KI fusion proteins containing tyrosine to phenylalanine mutations at various locations within the KI were expressed in E. coli and were either left in their non-phosphorylated state (lanes 1, 3, 5, 7, and 11) or were phosphorylated on tyrosine (lanes 2, 4, 6, 8, 10 and 12). Fusion proteins, immobilized with anti-TrpE antibodies and protein A-agarose, were incubated with Rat-2 cell lysates (FIG. 12A) The complexes were then analyzed for associated PI 3'-kinase activity. WT, wild-type insert (lanes 1 and 2); F697, Phe697 mutant (lanes 3 and 4); F706, Phe706 mutant (lanes 5 and 6); 2F, Phe697/Phe706 double mutant (lanes 7 and 8); F721, Phe721 mutant (lanes 9 and 10); 3F, Phe697/Phe706/Phe721 triple mutant (lanes 11 and 12). Anti-TrpE immunoprecipitates were also subjected to Western blotting analysis with either anti-phosphotyrosine antibodies (αP. Tyr) (FIG. 2B), or anti-TrpE antibodies (C) followed by [$^{125}$I]protein A. As shown in FIG. 13C, equivalent amounts of TrpE fusion proteins were isolated in each case.

The results in FIG. 13 show that TrpE-KI proteins with Phe at positions 697 (F697) or 706 (F706), or with Phe at both 697 and 706 (2F), were more highly tyrosine phosphorylated than the wild-type (WT) fusion protein (FIG. 13B), and bound concomitantly more PI 3'-kinase when incubated with a Rat-2 cell lysate (FIG. 13A). However, the Phe721 mutant TrpE-KI (F721), although it was still tyrosine phosphorylated, was defective in PI 3'-kinase association. A TrpE-KI protein with Phe at positions 697, 706 and 721 (3F) did not become detectably tyrosine phosphorylated and failed to bind PI 3'-kinase. These results suggest that phosphorylation of Tyr721 allows the bacterial fusion protein to bind PI 3'-kinase.

Figure 14:
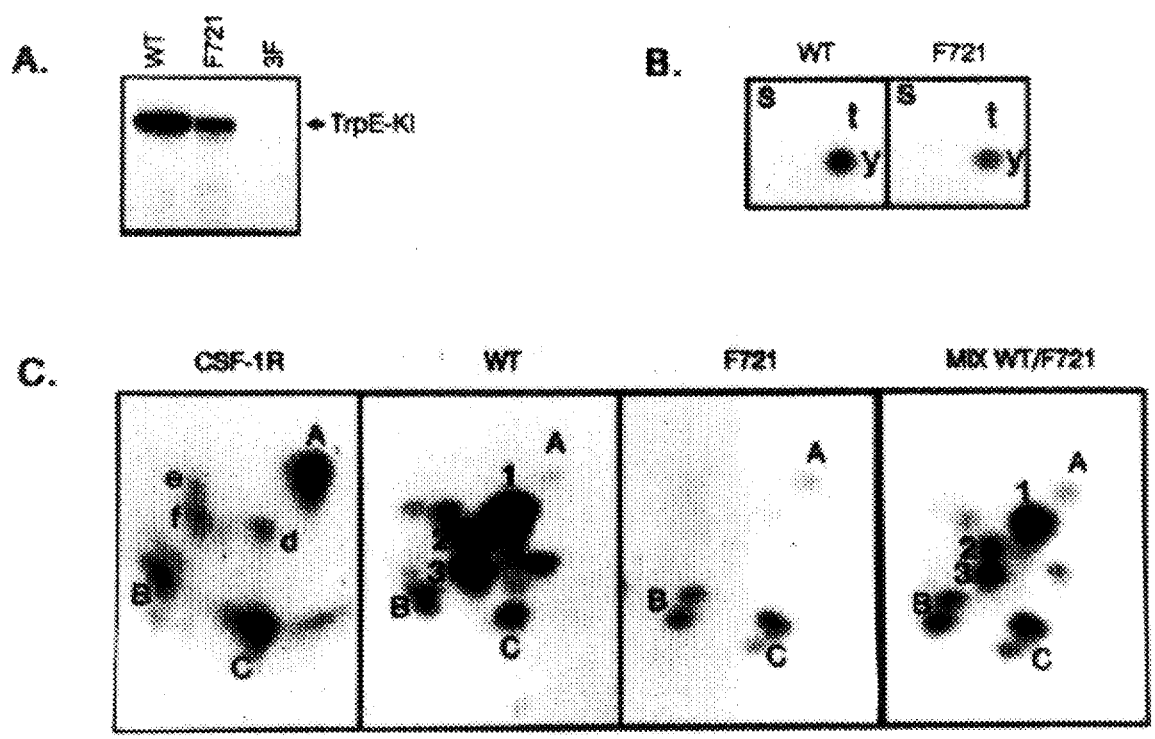
FIGS. 14A–14C show immunoblots of WT, F721, or 3F TrpE-KI fusion proteins immunoprecipitated from lysates of $^{32}$P-labelled bacteria following inducation of the Elk tyrosine kinase (A); phosphoamino acid analysis (B); and two-dimensional tryptic phosphopeptide analysis (C) of $^{32}$P-Labelled WT and F721 TrpE-KI fusion proteins.

To investigate which tyrosine residues were phosphorylated in the WT and mutant bacterial proteins, TrpE-KI proteins were immunoprecipitated from lysates of $^{32}$P-labelled bacteria, following induction of the Elk tyrosine kinase, and subjected to both phosphoamino acid analysis and two-dimensional tryptic phosphopeptide analysis. In particular, bacterial cultures containing WT, F721, or 3F TrpE-KI proteins and the λB1-Elk tyrosine kinase were labelled with $^{32}$p; lysed, and immunoprecipitated with 2 µg of monoclonal anti-TrpE antibodies bound to goat anti-mouse IgG agarose (FIG. 14A). The bound proteins were separated on a 12% SDS-polyacrylamide gel and analyzed by autoradiography. $^{32}$P-Labelled WT and F721 TrpE-KI fusion proteins were subjected to phosphoamino acid analysis (FIG. 14B). The positions of unlabelled phosphoserine (S), phosphothreonine (T) and phosphotyrosine (Y) markers are indicated in FIG. 14. $^{32}$P-Labelled WT and F721 TrpE-KI fusion proteins, phosphorylated by the Elk tyrosine kinase in E. coli were also digested with trypsin (FIG. 14C).

In addition, the full-length CSF-1 was autophosphorylated in vitro with [γ-$^{32}$P]ATP and subjected to trypsin digestion. The resulting tryptic phosphopeptides were separated by electrophoresis at pH 2.1 followed by ascending chromatography, and identified by autoradiography.

The results shown in FIG. 14 indicate that both the WT and F721 proteins were phosphorylated exclusively on tyrosine, whereas the 3F mutant did not become $^{32}$P-labelled (FIG. 14A and B). The WT TrpE-KI gave three major tryptic phosphopeptides (labelled 1,2 and 3 in FIG. 14C), and several minor ones, including those identified as A, B and C. The major spots 1–3 were lost in the F721 TrpE-KI (FIG. 14C), but were present in maps of the other mutant proteins (F697, F706, 2F;), suggesting that these spots represent peptides containing phosphorylated Tyr721. Tyr721 is flanked on its N-terminal side by two adjacent arginine residues (Arg708, Arg709), and on its C-terminal side by an arginine (Arg725) followed by proline, differential tryptic cleavage at these basic residues could account for the multiple spots apparently containing phosphorylated Tyr721. Peptide 1 of WT TrpE-KI co-migrated with a minor spot (peptide d) in a tryptic digest of autophosphorylated mouse CSF-1R, raising the possibility that Tyr721 may be a minor autophosphorylation site of the activated full-length receptor in vitro. Phosphopeptides A, B and C were minor spots in WT (FIG. 14C), but became more apparent in F721. Peptide A was absent from a digest of the F706 protein suggesting that this peptide contains phosphorylated Tyr706. Spots B and C were missing in the map of the F697 protein, indicating that these spots are derived from a Tyr697-containing phosphopeptide. Furthermore, peptides A, B and C from the F721 protein co-migrated with phosphopeptides from autophosphorylated mouse CSF-1R (FIG. 14C) that have been previously shown to contain Tyr706 (spot A) and Tyr697 (spots B and C) (Tapley et al., Mol. Cell. Biol. 10, 2528–2538 (1990); van der Geer and Hunter, Mol. Cell. Biol. 10, 2991–3002 (1990)). These results confirm that phosphorylation of Tyr721 in bacteria endows TrpE-KI with the ability to bind PI 3'-kinase, whereas phosphorylation of Tyr697 and Tyr706 does not contribute to PI 3'-kinase binding.

Example 9

Binding of p85 SH2 domains to the CSF-1R KI is regulated by phosphorylation of Tyr721.

Figure 15:
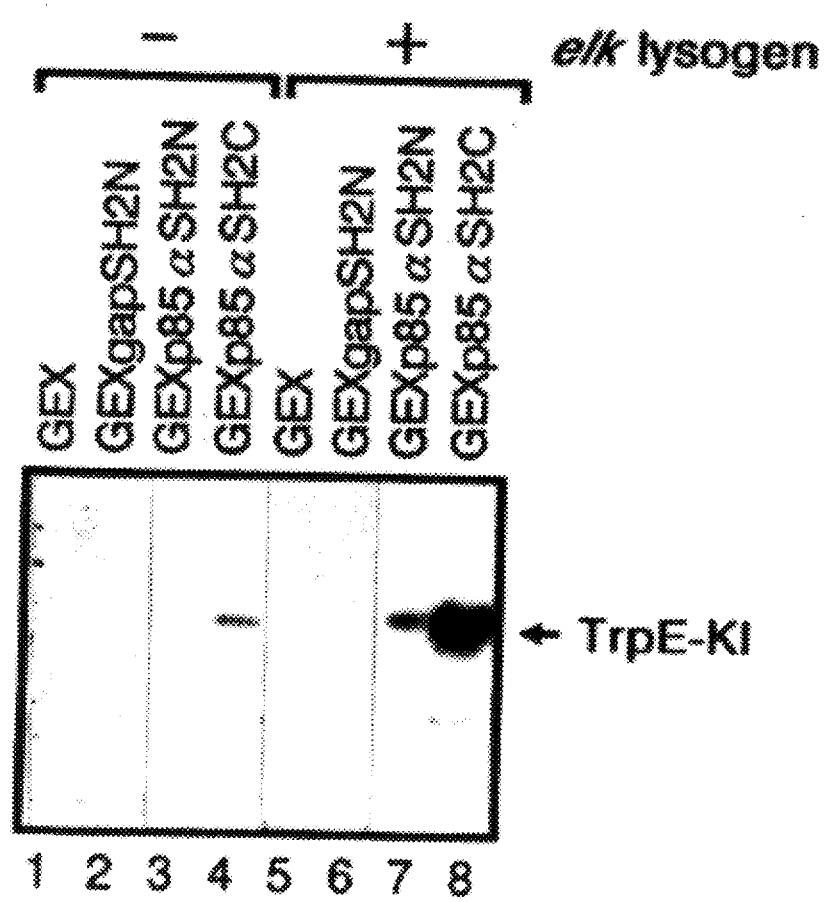
FIG. 15 shows immunoblots of immobilized GST SH2-fusion proteins mixed with lysates of bacteria expressing the TrpE-KI in its phosphorylated or unphosphorylated form.

Since the p85 SH2 domains are strong candidates for the elements that direct PI 3'-kinase association with activated receptors, the ability of p85α SH2 domains to bind the TrpE-KI polypeptide was tested. The N-terminal (N) and C-terminal (C) p85α SH2 domains were independently expressed in E. coli as glutathione Stransferase (GST) fusion proteins, and immobilized by attachment to glutathione-agarose beads. The immobilized GST-SH2 fusion proteins were then incubated with lysates of bacteria expressing the TrpE-KI in its phosphorylated or unphosphorylated form. The complexes were washed, and then analyzed by immunoblotting with anti-TrpE antibodies to detect any TrpE-KI that had associated with the PI 3'-kinase GST-SH2 fusion proteins. In particular, bacteria expressing GST alone (GEX; FIG. 15 lanes 1 and 5), or GST fusion proteins containing the N-terminal GAP SH2 domain (GEXgapSH2N; FIG. 15 lanes 2 and 6), the N-terminal p85α SH2 domain (GEXp85αSH2N; FIG. 15 lanes 3 and 7), and the C-terminal p85α SH2 domain (GEXp85αSH2C; FIG. 15 lanes 4 and 8) were lysed, and the GST fusion proteins were collected on glutathione-agarose beads. The beads were resuspended in lysates from bacteria expressing WT TrpE- KI either in its phosphorylated (FIG. 15 lanes 5-8) or non-phosphorylated (FIG. 15 lanes 1-4) form. After 1.5 hours incubation at 4° C., the beads were washed and associated proteins were electrophoresed through a 12.5% SDS-polyacrylamide gel. Proteins were transferred to nitrocellulose and probed with a αTrpE antibodies, followed by [$^{125}$I]protein A to detect SH2-associated TrpE-KI fusion proteins.

Figure 16:
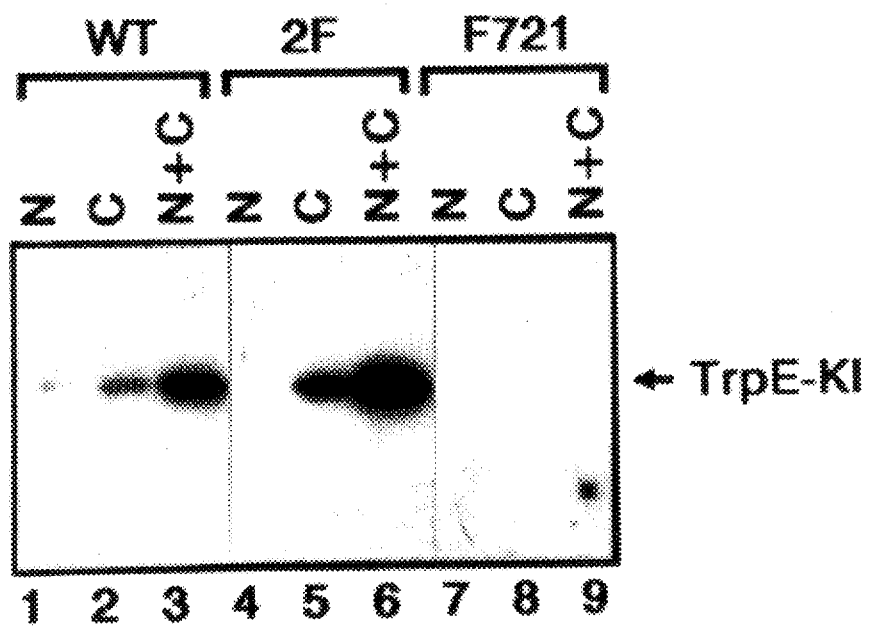
FIG. 16 shows immunoblots of immobilized fusion proteins encoded by GEXp85αSH2N, GEXp85αSH2C and GEXp85αSH2N+C (GST fused to both p85α SH2 domains); mixed with lysates of bacteria expressing the TrpE-KI in its phosphorylated or unphosphorylated form.

As shown in FIG. 15, very little of the unphosphorylated TrpE-KI protein complexed with the immobilized p85α SH2 fusion proteins. However, tyrosine phosphorylation of the TrpE-KI induced marked binding to the p85α SH2 domains. The C-terminal p85α SH2 domain consistently complexed more efficiently with the phosphorylated TrpE-KI than did the N-terminal SH2 domain. A fusion protein containing both the N and C SH2 domains (N+C) bound the tyrosine phosphorylated KI with greater affinity than did either the N or C SH2 domains alone (FIG. 16).

In contrast to the SH2 domains of PI 3'-kinase, no complex formation was observed between the N-terminal GAP SH2 domain and the CSF-1R KI, even when the latter was tyrosine phosphorylated. This is consistent with the observation that GAP does not bind efficiently to the CSF-1R in vivo (Reedijk et al., Mol. Cell. Biol. 10, 5601-5608 (1990)).

The importance of CSF-1R Tyr721 in the binding of P85α SH2 domains was investigated by incubating GST fusion proteins containing the N- or C-terminal SH2 domains, or both SH2 domains together, with lysates of bacteria expressing either the WT, 2F or F721 TrpE-KI proteins in their tyrosine phosphorylated forms. In particular, fusion proteins encoded by GEXp85αSH2N (FIG. 16 lanes 1, 4 and 7), GEXp85αSH2C (FIG. 16 lanes 2, 5 and 8) and GEXp85αSH2N+C (GST fused to both p85α SH2 domains; FIG. 16 lanes 3, 6 and 9) were immobilized on glutathione-agarose beads. The beads were resuspended in lysates of bacteria expressing λB1-Elk in combination with either WT TrpE-KI (FIG. 16 lanes 1-3), 2F (FIG. 16 lanes 4-6) or F721 (FIG. 16 lanes 7-9). The association of the WT or mutant forms of the KI with p85α SH2 domains were analyzed by immunoblotting with anti-TrpE antibodies, followed by [$^{125}$I]protein A.

The 2F TrpE-KI mutant, in which Tyr697 and Tyr706 are replaced by Phe, bound the p85α SH2 domains with an efficiency similar to that of the WT KI. In contrast, the F721 TrpE-KI mutant did not bind detectable amounts of p85α SH2 domains. This result is in agreement with the observation that F721 was severely reduced in its ability to complex with PI 3'-kinase activity in vitro (FIG. 13) and in vivo (see below).

Example 10

Binding of PI 3'-kinase to the CSF-1R in CSF-1-stimulated cell is dependent on Tyr721.

Figure 17:
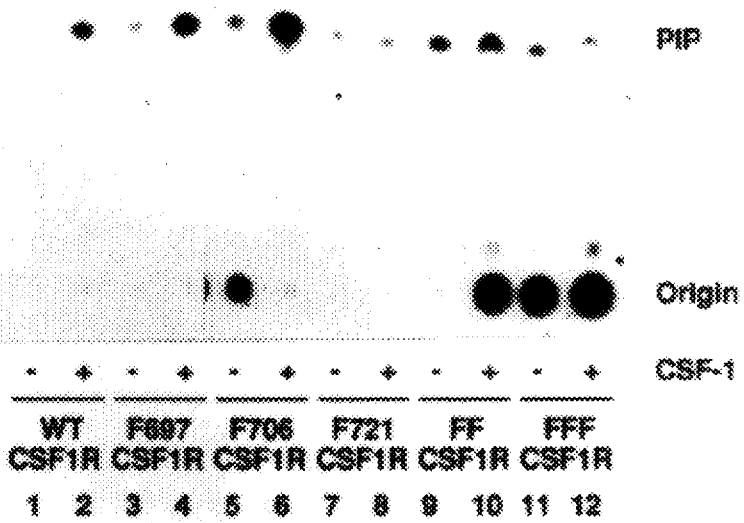
FIGS. 17A and 17B show immunoblots of immunoprecipitates of WT or mutant CSF-1R receptors from CSF-1 stimulated and control cells mixed with Rat-2 cells expressing PI 3'-kinase (A) and immunoblots of receptor immunoprecipitates mixed with anti-CSF-1R antibodies.
Figure 17:
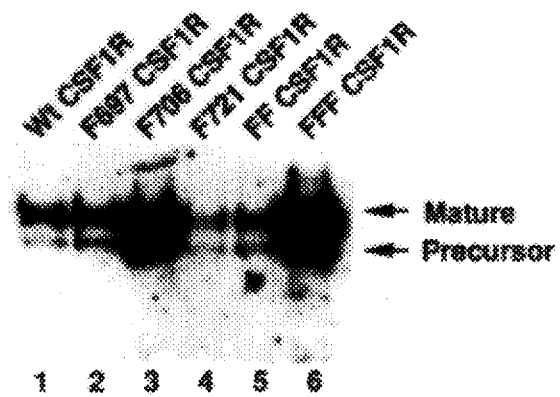

The possible role of different tyrosine autophosphorylation sites in the association of the CSF-1R with PI 3'-kinase mouse in vivo was studied by expressing WT and mutant CSF-1R cDNAs in 208 rat fibroblasts. Mutations which convert the codons for CSF-1R Tyr697, Tyr706 and Tyr721, either alone or in combination, were introduced into a full-length CSF-1 cDNA. A retroviral vector was then employed to obtain stable cell lines expressing the WT or mutant receptors. These cells were serum-starved for 48 hours, and then stimulated with recombinant human CSF-1 (rhCSF-1R). CSF-1R immunoprecipitates from control and CSF-1-stimulated cells were tested for associated PI 3'-kinase activity (FIG. 17A). In particular, wild-type (WT) or mutant CSF-1R cDNAs were stably expressed in rat fibroblasts as described above. Confluent 10 cm tissue culture dishes of 208F cells expressing WT and mutant CSF-1R cDNAs were starved in DMEM plus 10 mM HEPES, pH 7.4, and stimulated with 100 ng/ml rhCSF-1 for 3 minutes at 37° C. CSF-1R immunoprecipitates from control cells (FIG. 17A lanes 1, 3, 5, 7, 9 and 11) and CSF-1 stimulated cells (FIG. 17A lanes 2, 4, 6, 8, 10 and 12) were tested for associated PI 3'-kinase activity (van der Geer and Hunter, Mol. Cell. Biol. 10, 2991-3002 (1990)).

To control for CSF-1 levels, receptor immunoprecipitates from parallel dishes were analyzed by immunoblotting with an anti-CSF-1 serum (FIG. 17B). Receptor immunoprecipitates obtained from parallel dishes were separated by SDS-PAGE, transferred to Immobilon P and immunoblotted with anti-CSF-1R antibodies to quantify CSF-1R levels as described in van der Geer and Hunter, Mol. Vol. Biol. 11, 4698-4709 (1991). (PIP, phosphatidylinositol monophosphate) (FIG. 17B).

Whereas WT, F697, F607 and 2F (F697, F706) mutant receptors all associated with PI 3'-kinase upon stimulation with CSF-1, the F721 and 3F (F697, F706,F721) mutant receptors failed to do so. These results confirm the in vitro association data, and suggest that Tyr721 in the murine CSF-1R is essential for CSF-1-dependent association of the receptor with PI 3'-kinase in vivo.

We claim:

1. A method for assaying a medium for the presence of a substance that affects a Src homology region 2-phosphorylated ligand regulatory system comprising the steps of:

(a) providing a Src homology region 2, and a phosphorylated ligand, the Src homology region 2 and the phosphorylated ligand being selected so that they bind to form a Src homology region 2-phosphorylated ligand complex, the Src homology region 2 and/or the phosphorylated ligand being present in a known concentration;

(b) incubating said Src homology region 2 and said phosphorylated ligand with a test substance, under conditions which permit the formation of the Src homology region 2-phosphorylated ligand complex;

(c) assaying for the Src homology region 2-phosphorylated ligand complex, free Src homology region 2, or non-complexed phosphorylated ligand; and (d) comparing to a control to determine the effect of the substance.

2. A method for assaying a medium for the presence of an agonist or antagonist substance of a Src homology region 2-phosphorylated ligand regulatory system comprising the steps of:

(a) providing a Src homology region 2, and a phosphorylated ligand, the Src homology region 2 and the phosphorylated ligand being selected so that they bind to form a Src homology region 2-phosphorylated ligand complex which is capable of activating the Src homology region 2-phosphorylated ligand regulatory system, the Src homology region 2 and/or the phosphorylated ligand being present in a known concentration;

(b) incubating said src homology region 2 and said phosphorylated ligand with a suspected agonist or antagonist substance, under conditions which permit the formation of the Src homology region 2-phosphorylated ligand complex; and (c) assaying for the Src homology region 2-phosphorylated ligand complex, free Src homology region 2, or non-complexed phosphorylated ligand and comparing to a control to determine the effect of the substance.

3. A method as claimed in claim 1, wherein the phosphorylated ligand is a phosphotyrosine or phosphoserine/phosphothreonine polypeptide or peptide.

4. A method as claimed in claim 2, wherein the phosphorylated ligand is a phosphotyrosine or phosphoserine/phosphothreonine polypeptide or peptide.

5. A method as claimed in claim 1 or 2, wherein the substance assayed for affects a Src homology region 2-phosphorylated ligand regulatory system which regulates transformation pathways.

6. A method for assaying a medium for the presence of a substance that affects a Src homology region 2-phosphorylated ligand regulatory system comprising the steps of:

(a) providing a Src homology region 2, and a phosphorylated ligand which is a Src homolog region 2 binding site on a transmembrane receptor with inducible protein-tyrosine kinase activity or on a deregulated protein-tyrosine kinase, the Src homology region 2 and the phosphorylated ligand being selected so that they bind to form a Src homology region 2-phosphorylated ligand complex, the Src homology region 2 and/or the phosphorylated ligand being present in a known concentration;

(b) incubating said Src homology region 2 and said phosphorylated ligand with a test substance, under conditions which permit the formation of the Src homology region 2-phosphorylated ligand complex;

(c) assaying for the Src homology region 2-phosphorylated ligand complex, free Src homology region 2, or non-complexed phosphorylated ligand; and (d) comparing to a control to determine the effect of the substance.

7. A method for assaying a medium for the presence of an agonist or antagonist substance of a Src homology region 2-phosphorylated ligand regulatory system, comprising the steps of:

(a) providing a Src homology region 2, and a phosphorylated ligand which is a Src homology region 2 binding site on a transmembrane receptor with inducible protein-tyrosine kinase activity or on a deregulated protein-tyrosine kinase, the Src homology region 2 and the phosphorylated ligand being selected so that they bind to form a Src homology region 2-phosphorylated ligand complex which is capable of activating the Src homology region 2phosphorylated ligand regulatory system, the Src homology region 2 and/or the phosphorylated ligand being present in a known concentration;

(b) incubating said src homology region 2 and said phosphorylated ligand with a suspected agonist or antagonist substance, under conditions which permit the formation of the Src homology region 2-phosphorylated ligand complex;

(c) assaying for the Src homology region 2-phosphorylated ligand complex, free Src homology region 2, or non-complexed phosphorylated ligand; and (d) comparing to a control to determine the effect of the substance.

8. A method for screening for a phosphorylated ligand which is active in an SH2-phosphorylated ligand regulatory system comprising the steps of:

(a) selecting an SH2 domain which is active in the SH2-phosphorylated ligand regulatory system;

(b) reacting the SH2 domain with a phosphorylated ligand which is suspected of being capable of binding to the SH2 domain thereby activating the SH2-phosphorylated ligand regulatory system, under conditions which permit the SH2 domain and phosphorylated ligand to bind to form an SH2-phosphorylated ligand complex;

(c) determining the mount of SH2-phosphorylated ligand complex, free SH2 domain, or non-complexed phosphorylated ligand; and (d) comparing in a control to determine if the phosphorylated ligand binds to Src homology region 2 domains.

9. A method as claimed in claim 1 or 2, wherein the phosphorylated ligand is a Src homology region 2 binding site on a transmembrane receptor with inducible protein-tyrosine kinase activity.

10. A method as claimed in claim 1 or 2, wherein the phosphorylated ligand is a Src homology region 2 binding site on epidermal growth factor receptor or the platelet-derived growth factor receptor.

* * * * *